(12) United States Patent
Park et al.

(10) Patent No.: US 8,906,346 B2
(45) Date of Patent: *Dec. 9, 2014

(54) MRI CONTRAST AGENT FOR LYMPHOGRAPHY BASED ON IRON OXIDE NANOPARTICLES AND METHOD FOR IMAGING LYMPH NODE USING THE SAME

(75) Inventors: Ju Young Park, Daejeon (KR); Wan Jae Myeong, Daejeon (KR); Bong-Sik Jeon, Daejeon (KR); Eung Gyu Kim, Daejeon (KR); Eun Byul Kwon, Daejeon (KR); Taeghwan Hyeon, Seoul (KR); Daishun Ling, Seoul (KR)

(73) Assignee: Hanwha Chemical Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,301

(22) PCT Filed: Jun. 20, 2012

(86) PCT No.: PCT/KR2012/004861
§ 371 (c)(1),
(2), (4) Date: Sep. 23, 2013

(87) PCT Pub. No.: WO2012/177039
PCT Pub. Date: Dec. 27, 2012

(65) Prior Publication Data
US 2014/0023594 A1    Jan. 23, 2014

(30) Foreign Application Priority Data
Jun. 22, 2011  (KR) .................. 10-2011-0060438

(51) Int. Cl.
*A61K 49/04*    (2006.01)
*A61K 49/12*    (2006.01)
*A61K 49/18*    (2006.01)
*B82Y 15/00*    (2011.01)

(52) U.S. Cl.
CPC .......... *A61K 49/124* (2013.01); *A61K 49/1857* (2013.01); *A61K 49/186* (2013.01); *B82Y 15/00* (2013.01)
USPC .................. 424/9.4; 424/9.42; 424/78.17

(58) Field of Classification Search
None
See application file for complete search history.

(56) References Cited

U.S. PATENT DOCUMENTS

| 2002/0012698 A1* | 1/2002 | Bauerlein et al. ............. 424/450 |
| 2008/0253960 A1* | 10/2008 | Zheng et al. ................ 424/1.11 |
| 2009/0280063 A1 | 11/2009 | Kulkarni et al. |
| 2013/0272965 A1* | 10/2013 | Hyeon et al. .................. 424/9.3 |

FOREIGN PATENT DOCUMENTS

EP    2 289 553 A1    3/2011

OTHER PUBLICATIONS

Tsai et al., "Dopamine-assisted immobilization of poly(ethylene imine) based polymers for control of cell-surface interactions," Acta Biomaterialia, 2011, vol. 7, pp. 2518-2525.
Dalsin et al., "Protein Resistance of Titanium Oxide Surfaces Modified by Biologically Inspired mPEG-DOPA," Langmuir, 2005, vol. 21, pp. 640-646.
Xu et al., "Dopamine as A Robust Anchor to Immobilize Functional Molecules on the Iron Oxide Shell of Magnetic Nanoparticles," J. Am. Chem. Soc., 2004, vol. 126, pp. 9938-9939.
Dalsin et al., "Mussel Adhesive Protein Mimetic Polymers for the Preparation of Nonfouling Surfaces," J. Am. Chem. Soc., 2003, 125, 4253-58.
International Searching Authority, International Search Report of PCT/KR2012/004861, dated Jan. 29, 2013.

* cited by examiner

*Primary Examiner* — James Rogers
(74) *Attorney, Agent, or Firm* — Sughrue Mion, PLLC

(57) ABSTRACT

Provided are a contrast agent for contrast imaging lymph node, which includes iron oxide nanoparticles dispersed and stabilized in an aqueous medium by a mussel adhesive protein-mimetic copolymer, a method for contrast enhanced lymphography using the foregoing contrast agent, and a method for diagnosis of lymph node cancers using the foregoing contrast agent. Using such a mussel adhesive protein-mimetic copolymer, the surface of iron oxide is modified and dispersed well in water to prepare a colloidal solution, which in turn forms the contrast agent containing the colloidal solution. The inventive contrast agent does not have toxicity and is easily taken up to the lymph node to exhibit excellent contrast imaging effects. The contrast agent of the present invention is useful for diagnosis of metastatic cancers.

12 Claims, 14 Drawing Sheets

FIGURE. 1
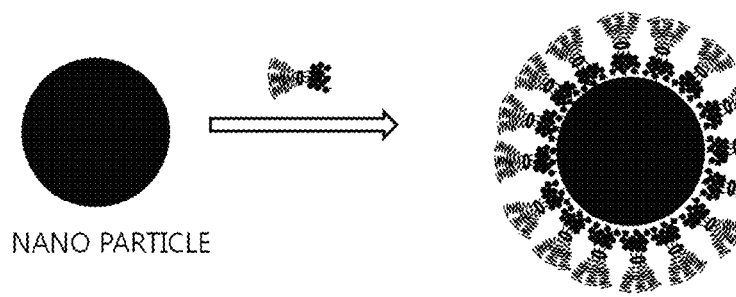
NANO PARTICLE
POLYETHYLEGLYCOL   POLYETHYLENIMINE   PDOPA
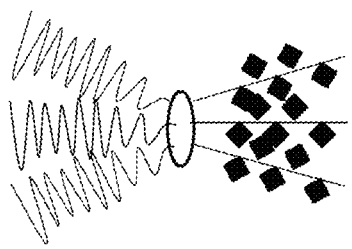
MUSSEL ADHESIVE PROTEIN MIMETIC COPOLYMER
(Polyethyleneimine-*graft*-
(Polyethyleneglycol;Poly3,4-dihydroxyphenylalanine))
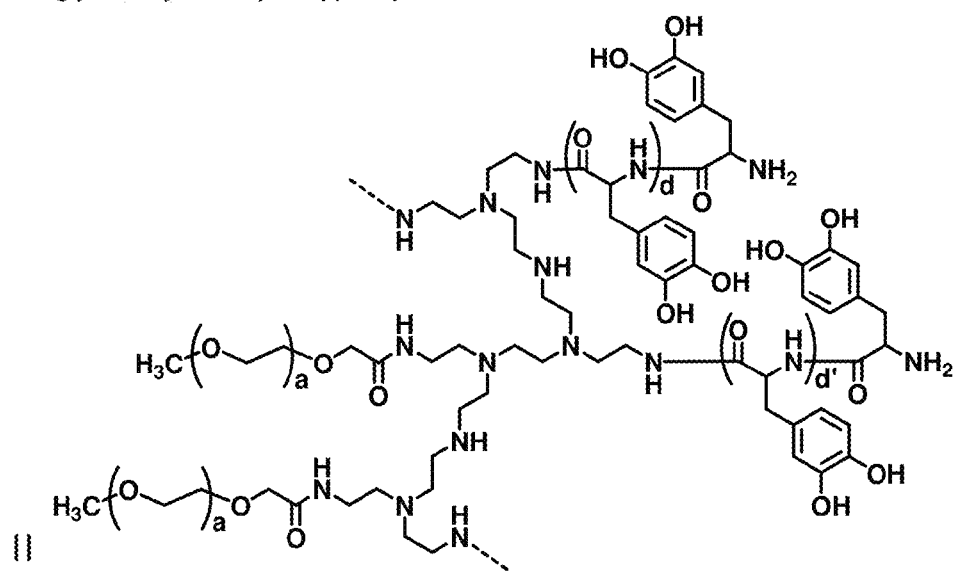

FIGURE 13
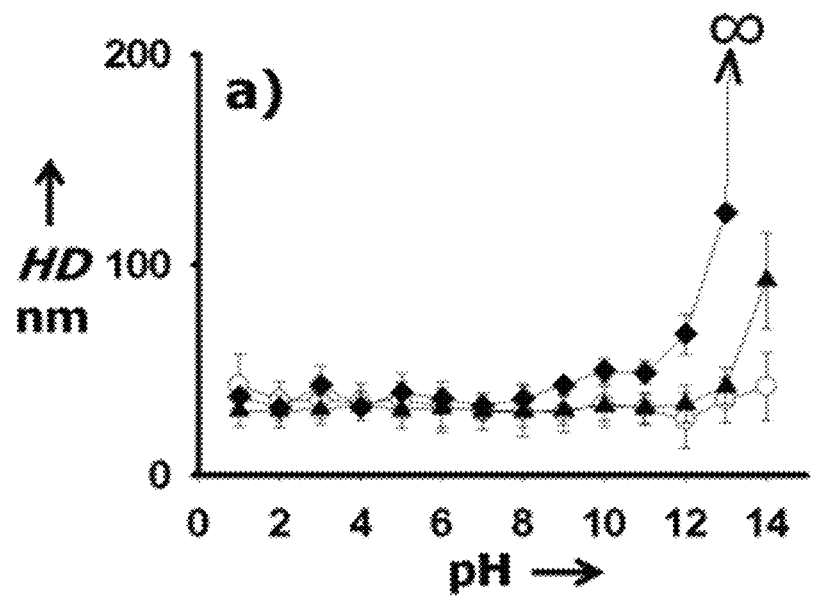
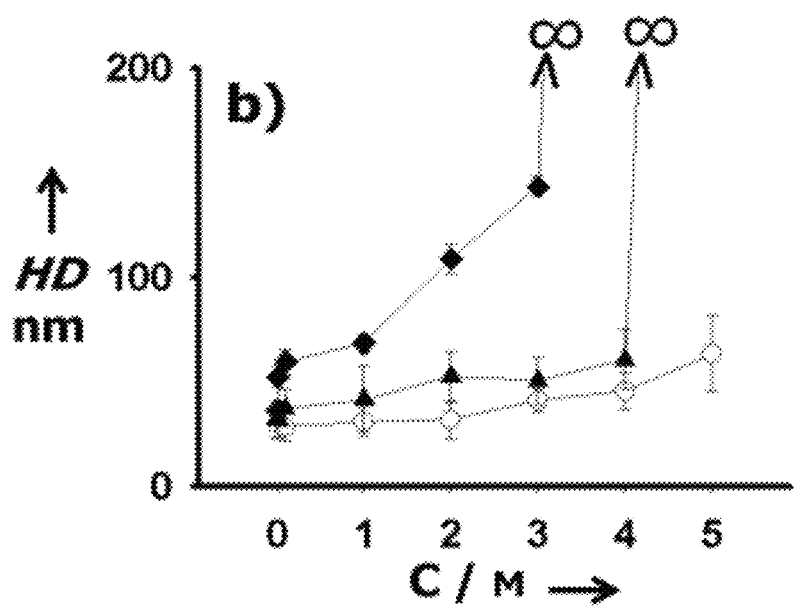

MRI CONTRAST AGENT FOR LYMPHOGRAPHY BASED ON IRON OXIDE NANOPARTICLES AND METHOD FOR IMAGING LYMPH NODE USING THE SAME

CROSS REFERENCE TO RELATED APPLICATIONS

This application is a National Stage of International Application No. PCT/KR2012/004861 filed Jun. 20, 2012, claiming priority based on Korean Patent Application No. 10-2011-0060438 filed Jun. 22, 2011, the contents of all of which are incorporated herein by reference in their entirety.

TECHNICAL FIELD

The present invention relates to a contrast agent for contrast enhanced lymphography, which includes iron oxide nanoparticles dispersed and stabilized in an aqueous medium by a mussel adhesive protein-mimetic copolymer, as well as a method for contrast enhanced lymphography using the same. More particularly, the mussel adhesive protein-mimetic copolymer is a polyethyleneimine-graft-(polyethyleneglycol;poly-3,4-dihydroxyphenylalanine) (PEI-graft-(PEG; PDOPA)). The graft polymer is composed of two parts, one is including polyethyleneimine grafted with a polyethyleneglycol-based biocompatible polymer, which has an affinity to an aqueous medium (sometimes, abbrev. to 'polyethyleneglycol grafted polyethyleneimine'), and the other is poly-3,4-dihydroxyphenylalanine (PDOPA), which has an affinity to the surface of nanoparticles. The present invention relates to a contrast agent for contrast enhanced lymphography, which includes a colloidal solution prepared by modifying the surface of iron oxide particles using the foregoing mussel adhesive protein-mimetic copolymer and then dispersing the particles in water. The present invention relates to a method for contrast enhanced lymphography using the contrast agent.

BACKGROUND ART

Nanoparticles are used in a broad range of applications such as nano-electronic convergence technology, in vivo imaging technology, medical applications, etc. Specifically, super-paramagnetic iron oxide nanoparticles are widely used in a variety of biomedical applications including, for example, a magnetic resonance imaging ('MRI') contrast agent, cell therapy, hyperthermia, drug delivery, cell separation, nucleic acid preparation, or the like.

The most important requirement for application in biomedical applications is primarily to ensure high quality nanoparticles and, in addition, to allow nanoparticles to have excellent dispersibility and stability in an aqueous medium. Here, the high quality nanoparticle may mean nanoparticles with features of; (i) uniformity of particle size, (ii) easy control of particle size, (iii) particle crystallinity, (iv) possibility in controlling particle morphology, etc. However, nanoparticles commercially available in the art are mostly synthesized in an aqueous system or may be obtained by synthesis in a gas phase. Nanoparticles generated by the foregoing processes have difficulty in preparing particles with a uniform shape and generally show low crystallinity. Further, it is difficult to manufacture nanoparticles having a uniform size and control the size of a particle.

Recently, numerous studies have been executed to develop a novel method for manufacturing metal oxide nanoparticles in an organic system, which have relatively high quality, that is, uniform size and favorable crystallinity, compared to nanoparticles synthesized in an aqueous system according to the related art.

As such, in the case where nanoparticles are synthesized in an organic solvent, uniformity and size control of the nanoparticles may sometimes be achieved by stabilization thereof using an organic additive during a synthesizing process. In this regard, since the surface condition of nanoparticles is influenced by a hydrophobic organic additive, the metal oxide nanoparticles may be easily dispersed in a hydrophobic organic solvent. However, when they are mixed with water, they do not have sufficient stability.

For such nanoparticles prepared in an organic solvent, hydrophobic properties of the surface of the nanoparticles may obscure stable dispersion of the nanoparticles in water, thus causing a problem for use in biomedical applications. Therefore, in order to use the nanoparticles in the foregoing applications, there is a need to develop a biocompatible dispersion stabilizer that reforms (or modifies) the surface of the nanoparticles in order to have hydrophilic properties and ensures a suitable condition so as to be homogeneously dispersed in an aqueous medium. In addition, development of a nanoparticle colloidal solution that is prepared using the biocompatible dispersion stabilizer described above, wherein the dispersion state is stably maintained in an aqueous system, is also required.

Among methods for dispersing nanoparticles in an aqueous system according to the techniques in the related art, use of a thin silica layer has currently been disclosed in the Journal of American Chemical Society, 2005, 127, 4990. According to the foregoing article, polyoxyethylene nonylphenylether is introduced to a cyclohexane solution and mixed with the same to form micro-micelle emulsion drops. Next, a sol-gel reaction of tetraethyl ortho-silicate (TEOS) is induced and nanoparticles are coated with a silica layer and dispersed in water. The above document described a process of coating the outer side of the nanoparticles with a hydrophilic silica layer to disperse the nanoparticles in water, wherein the nanoparticles were prepared in an organic solvent. In this case, the silica coating method using micro-emulsion entails a problem in that, since an amount of nanoparticles to be coated at just one time is very small, an amount of nanoparticle dispersion in an aqueous system manufactured in a single process is also greatly reduced. Moreover, according to the amount of nanoparticle colloids manufactured in the single process or an amount of polyoxyethylene nonylphenylether, the conditions of the micro-emulsion are altered. Therefore, there are difficulties in finely regulating a desired thickness of a silica layer, and attaining uniformity of the coated particles since the number of nanoparticles contained in the silica layer is altered. In the case where nanoparticles are stabilized by a silica layer, the foregoing techniques in the related art entail problems in that silane functional groups on the surface of the silica are not sufficiently stable but react to one another, therefore, the nanoparticles coated with the silica and dispersed in water were combined and became agglomerated over time. As a result, it was difficult to ensure storage stability of the dispersion over a long period of time.

In recent years, a method for dispersing nanoparticles in water using a polymer composed of phosphine oxide and polyethyleneglycol has been disclosed in the Journal of America Chemical Society (2005, 127, 4556). More particularly, the foregoing article described a nanoparticle dispersing method wherein, after reacting polyethyleneglycol with 1,2-bis(dichlorophosphino)ethane to synthesize a polymer having polyethyleneglycols bonded together, the polymer is subjected to a ligand exchange reaction with nanoparticles dispersed in a hydrophobic solvent, thereby enabling dispersion stabilization of the nanoparticles and uniformly dispersing the same in water. The disclosed method uses a simple preparation method and utilizes ligand exchange to disperse nanoparticles in water. However, since phosphorus atom (P) is likely to oxidize and become a phosphoryl group, a coating polymer must be synthesized in an inert atmosphere using nitrogen or argon. Further, since the polymer is in a cross-linked state, a problem in introducing a functional group to bond functional ligands in vivo such as DNA, RNA, a monoclonal antibody or other functional proteins, still remains.

Scientists have recently conducted a number of studies upon mussels as a potential origin of bio-adhesives. Mussels generate and secrete a sticky material which is functionally differentiated to allow the mussels to be stationary or anchor in the water, in a marine environment having characteristics of salinity, humidity, tidal flow, turbulent flow, waves, etc. The mussel strongly adheres to the surface of a material in water, using threads composed of a fiber bundle secreted from legs thereof. At the end of each fiber, a plaque comprising a water-proof adhesive is present to allow the mussel to adhere to a wet solid surface. Such thread protein contains a large quantity of 3,4-dihydroxyphynyl-L-alanine (DOPA), which is an amino acid obtained by hydroxylation of tyrosine groups using a polyphenol oxidase. 3,4-dihydroxyphenyl (catechol) on a side branch of DOPA may create a very strong hydrogen bond with the hydrophilic surface and/or be strongly bonded with metal ions, metal oxides ($Fe^{3+}$, $Mn^{3+}$), semi-metal (silicon), or the like.

Occurrence of a metastatic cancer decisively influences prognosis and treatment of a cancer. The occurrence of a metastatic cancer may be determined by presence or absence of lymph node metastasis and occurrence of a metastatic lymph node cancer is currently diagnosed by surgically biopsying the lymph node. However, this is an invasive method involving significant difficulties to both a patient and a physician. On the other hand, non-invasive techniques such as use of CT, MRI, PET, etc. may be employed to detect occurrence of a metastatic cancer, but, incurs a problem in that cancer may generally be detected when its size is 5 mm or more. Accordingly, there is still a need for a method capable of non-invasively diagnosing metastatic cancer having a relatively small size.

A method for detecting metastatic cancer by injecting iron oxide nanoparticles in vivo and using an magnetic resonance image to show iron oxide deposition on lymph nodes has been introduced (Mukesh G. Harisinghani, M.D., Jelle Barentsz, M.D., Ph.D., Peter F. Hahn, M.D., Ph.D., Willem M. Deserno, M.D., Shahin Tabatabaei, M.D., Christine Hulsbergen van de Kaa, M.D., Ph.D., Jean de la Rosette, M.D., Ph.D., and Ralph Weissleder, M.D., Ph.D., and New England Journal of Medicine 2003; 348:2491-2499). According to the disclosed method, after stabilizing iron oxide nanoparticles in an aqueous system using a hydrophilic material, the treated nanoparticles are introduced in vivo and, after a predetermined time, lymph node tissues with cancer as well as normal lymph node tissues are observed through an MRI. Based on a difference in observed results therebetween, the occurrence of cancer may be diagnosed. Using the foregoing method, AMAG Co. (United States) has developed a MRI contrast agent named 'COMBIDEX' for contrast enhanced lymphography. However, the above contrast agent often causes adverse effects after in vivo administration and/or has poor selectivity, thus, is not widely used. Accordingly, there is still a need for developing an improved iron oxide-based contrast agent for contrast enhanced lymphography, having excellent selectivity and reduced adverse effects.

DISCLOSURE

Technical Problem

Therefore, as a result of intensive and extensive efforts to overcome the above problems in the related art, the present inventors have completed a biocompatible dispersion stabilizer that can reform the surface of nanoparticles into a hydrophilic state so as to disperse the nanoparticles in an aqueous system and have found that using the same (the stabilizer) may enable the nanoparticles to be dispersed and stabilized ('dispersion stabilization') in the aqueous system, thereby being effectively used for biomedical applications. In addition, it was also found that the nanoparticles dispersed and stabilized by the biocompatible dispersion stabilizer of the present invention may be applicable to a nano-electronic fusion technique field such as a quantum dot (Q-dot) light emitting device, a bio-imaging field such as a MRI contrast agent, a tissue engineering field such as cell therapy, a biomedical field such as hyperthermia, drug delivery, and so forth.

An object of the present invention is to provide a contrast agent for contrast enhanced lymphography, which includes iron oxide nanoparticles dispersed and stabilized in an aqueous medium by a mussel adhesive protein-mimetic copolymer, wherein the surface of various nanoparticles is reformed into a hydrophilic state through a simple process by mimicking mussel protein, so as to stabilize dispersion of the nanoparticles in an aqueous medium while enabling application thereof in biomedical fields.

Another object of the present invention is to provide a method for contrast enhanced lymphography using the foregoing contrast agent.

Another object of the present invention is to provide a method for diagnosing cancer of lymph nodes using the foregoing contrast agent.

Technical Solution

In one general aspect, the present invention provides a contrast agent for contrast enhanced lymphography, which includes iron oxide nanoparticles dispersed and stabilized in an aqueous medium by a mussel adhesive protein-mimetic copolymer, a method for contrast enhanced lymphography using the same, and a method for diagnosing cancer of lymph nodes using the same. More particularly, the mussel adhesive protein-mimetic copolymer is a polyethyleneimine-graft-(polyethyleneglycol;poly-3,4-dihydroxyphenylalanine) (PEI-graft-(PEG;PDOPA)), including polyethyleneimine grafted with a polyethyleneglycol-based biocompatible polymer having affinity to an aqueous medium (sometimes, abbrev. to 'polyethyleneglycol grafted polyethyleneimine'), and poly-3,4-dihydroxyphenylalanine (PDOPA) having affinity to the surface of nanoparticles. The present invention also provides a contrast agent for contrast enhanced lymphography, which includes a colloidal solution prepared by modifying the surface of iron oxide particles using the foregoing mussel adhesive protein-mimetic copolymer and then dispersing the particles in water, a method for contrast enhanced lymphography using the foregoing contrast agent, and a method for diagnosing cancer of lymph nodes using the foregoing contrast agent.

Hereinafter, the present invention will be described in more detail.

The mussel adhesive protein-mimetic copolymer used in the present invention is a polyethyleneimine-graft-(polyethyleneglycol;poly-3,4-dihydroxyphenylalanine) (PEI-graft- (PEG;PDOPA)), including polyethyleneimine grafted with a polyethyleneglycol-based biocompatible polymer having affinity to an aqueous medium (sometimes, abbrev. to 'polyethyleneglycol grafted polyethyleneimine'), and poly-3,4-dihydroxyphenylalanine (PDOPA) having affinity to the surface of nanoparticles, and contains a mussel adhesive amino acid, that is, 3,4-dihydroxyphynylalanine (DOPA).

In order to prepare the polyethyleneimine-graft-(polyethyleneglycol;poly-3,4-dihydroxyphenylalanine), polyethyleneglycol and polyethyleneimine are first combined through covalent bonding to form a polyethyleneimine-graft-polyethyleneglycol. The formed product is used as a biocompatible macro-initiator.

The polyethyleneglycol used herein may be polyethyleneglycol having a number average molecular weight of 300 to 50,000 and a hydroxyl group or carboxyl group at an end thereof. According to one embodiment of the present invention, the polyethyleneglycol is methoxy polyethyleneglycol carboxylic acid having a methoxy group at one end and a carboxyl group substituted at the other end.

The polyethyleneimine used herein may be a branched polyethyleneimine without toxicity, which has a number average molecular weight of 100 to 10,100, preferably 100 to 2,000. If the number average molecular weight of the branched polyethyleneimine is less than 100, the produced copolymer of the present invention cannot be suitably combined with a physiologically active material useful therefore. On the other hand, when the number average molecular weight is 10,100 or more, difficulties in excreting the above material out of the body through kidneys may be incurred. Accordingly, the present invention preferably uses polyethyleneimine having a number weight molecular weight present in the foregoing range.

The poly-3,4-dihydroxyphenylalanine (PDOPA) used in the present invention may be a condensation polymer which has 3,4-dihydroxyphynylalanine (DOPA) as a monomer. The repeating units are connected via amide bonds. The number of repeating units ranges from 1 to 100. The poly-3,4-dihydroxyphenylalanine (PDOPA) may be polymerized by solid phase synthesis and liquid phase synthesis using various coupling methods; carbodiimide-mediated reaction, a symmetrical anhydride method, a mixed anhydride method, an active ester method, an azide method, an acyl-chloride method and an N-carboxy anhydride method. Such example methods which are described hereinbefore are provided to offer a clear understanding of the poly-3,4-dihydroxyphenylalanine (PDOPA). However the poly-3,4-dihydroxyphenylalanine (PDOPA) are not limited to the polymers which are synthesized by the above methods. The poly-3,4-dihydroxyphenylalanine (PDOPA) used in the present invention may be prepared by the several methods described hereinbefore, preferably by the N-carboxy anhydride method.

The polyethyleneimine-graft-(polyethyleneglycol;poly-3,4-dihydroxyphenylalanine) used in the present invention may include; a polyethyleneglycol unit represented by the following structure (A), a polyethyleneimine unit represented by the following structure (B), and a poly-3,4-dihydroxyphenylalanine (PDOPA) unit represented by the following structure (C).

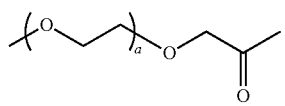

(A)

wherein a ranges from 2 to 1200.

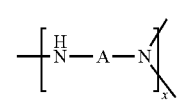

(B)

wherein A is a branched polyethyleneimine and x ranges from 1 to 100.

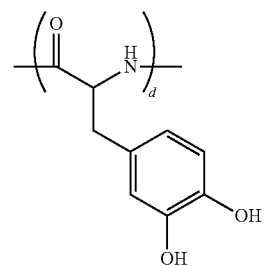

(C)

wherein d ranges from 1 to 100.

The above polyethyleneimine unit (B) may particularly be represented by the following structure.

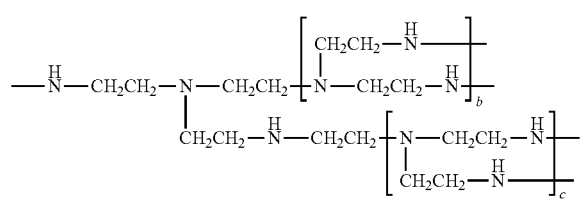

wherein b and c are each independently ranging from 1 to 100, preferably, 1 to 30. The poly-3,4-dihydroxyphenylalanine (PDOPA) used in the present invention is synthesized from N-carboxyl anhydride (NCA) of 3,4-dihydroxyphynylalanine (DOPA) wherein the DOPA is one of the mussel adhesive amino acids and preferably at least one selected from L-DOPA (L-3,4-dihydroxylphenylalanine) and D-DOPA (D-3,4-dihydroxylphenylalanine). The PDOPA may be selected from a group consisting of L-PDOPA synthesized from N-carboxyl anhydride (NCA) of L-DOPA (L-3,4-dihydroxylphenylalanine), D-PDOPA synthesized from N-carboxyl anhydride (NCA) of D-DOPA (D-3,4-dihydroxylphenylalanine) and L,D-PDOPA synthesized from N-carboxyl anhydride (NCA) of L,D-DOPA (L,D-3,4-dihydroxylphenylalanine, mixture of L-DOPA and D-DOPA).

The mussel adhesive protein-mimetic copolymer, that is, the polyethyleneimine-graft-(polyethyleneglycol;poly-3,4-dihydroxyphenylalanine) may be fabricated by the following operations:

(a) combining polyethyleneglycol as a hydrophilic polymer with polyethyleneimine through covalent bonding, to form a polyethyleneimine-graft-polyethyleneglycol; (b) after protecting hydroxyl groups of 3,4-dihydroxyphynylalanine (DOPA), synthesizing 3,4-dihydroxyphynylalanine N-carboxyl anhydride (DOPA-NCA) in the presence of a triphosgene catalyst; and (c) reacting the polyethyleneimine-graft-polyethyleneglycol prepared in operation (a) and the 3,4-dihydroxyphynylalanine N-carboxyl anhydride (DOPA-NCA) synthesized in operation (b) in an organic solvent, to thus prepare a polyethyleneimine-graft-(polyethyleneglycol; poly-3,4-dihydroxyphenylalanine).

Operation (a) is a process of preparing a biocompatible macro-initiator used for manufacturing a mussel adhesive protein-mimetic copolymer. In operation (a), covalent bonding of polyethyleneglycol and polyethyleneimine may be implemented using dicyclohexylcarbodiimide (DCC)/N-hydroxysuccinimide (NHS) or, otherwise, hexamethylene diisocyanate (HMDI). Here, DCC and NHS activate a carboxyl group in polyethyleneglycol having both methoxy and carboxyl group ends, in order to react with a primary amine of polyethyleneimine, thus forming a peptide covalent bond. Alternatively, HMDI activates a hydroxyl group of polyethyleneglycol having a methoxy end and serves to bond it to a primary amine of polyethyleneimine. Covalent bonding between polyethyleneglycol and polyethyleneimine activated by HMDI may include any reaction to form a covalent bond between the foregoing two polymers. In one embodiment of the present invention, after dissolving polyethyleneglycol and polyethyleneimine activated by DCC/NHS in chloroform, respectively, the polyethyleneglycol solution is added drop by drop to the polyethyleneimine solution, thus enabling these two polymers to be covalently bonded. After completing a reaction, the reacted solution is concentrated and precipitated in diethylether to produce a polyethyleneimine-graft-polyethyleneglycol in which polyethyleneglycol and polyethyleneimine are covalently bonded. A structure of polyethyleneglycol activated by DCC/NHS and a covalent bond structure of the activated polyethyleneglycol and a branch type polyethyleneimine (PEI) are illustrated as follows:

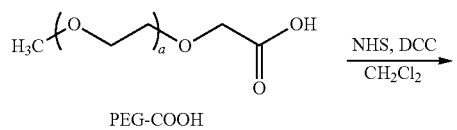

PEG-COOH

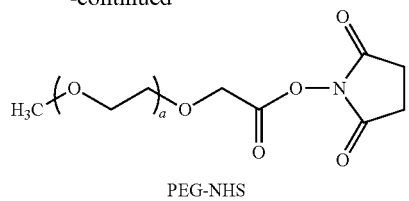

PEG-NHS

[wherein, a ranges from 2 to 1200.]

Activation of Polyethyleneglycol (PEG-NHS)

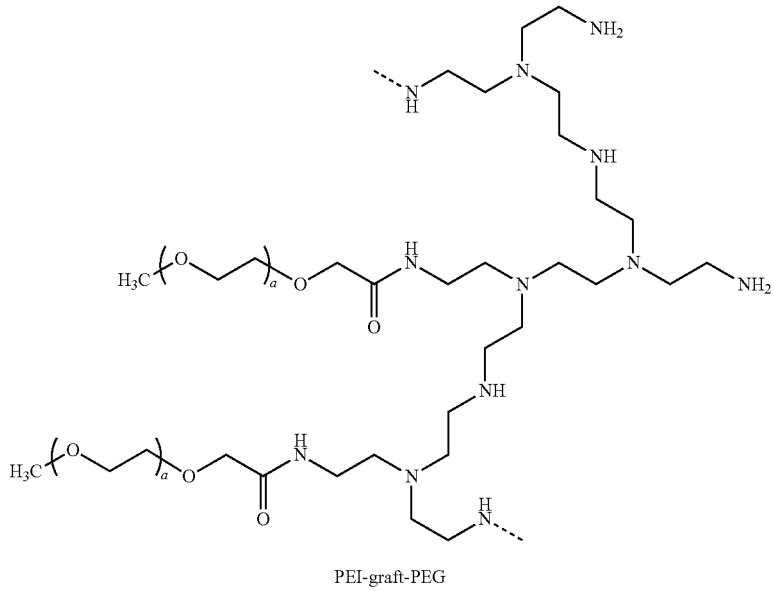

PEI-graft-PEG

[wherein, a ranges from 2 to 1200.]

Polyethyleneimine-graft-polyethyleneglycol (PEI-graft-PEG)

Synthesis of 3,4-dihydroxyphynylalanine N-carboxyl anhydride (DOPA-NCA) in operation (b) may be executed using at least one selected from the mussel adhesive amino acids, that is, L-DOPA (L-3,4-dihydroxylphenylalanine) and D-DOPA (D-3,4-dihydroxylphenylalanine) as a starting material and by any method for preparation of amino acid N-carboxyl anhydride (NCA) known in the related art. Preferably, the foregoing substance (NCA) is prepared by reacting the mussel adhesive amino acid (D-DOPA or L-DOPA or L,D-DOPA) in a proper solvent in the presence of a triphosgene catalyst.

According to one embodiment of the present invention, as illustrated below, DOPA is dissolved in acetic acid, using acetic acid anhydride as well as hydrochloric acid, followed by acetylation of a hydroxyl group of L-DOPA to synthesize (AC)$_2$-DOPA while protecting the hydroxyl group. Thereafter, using triphosgene in an organic solvent composed of tetrahydrofurane (THF), N-carboxyl anhydride (NCA) of DOPA is synthesized [see below].

Reaction Scheme of 3,4-dihydroxyphynylalanine N-carboxyl anhydride (DOPA-NCA)

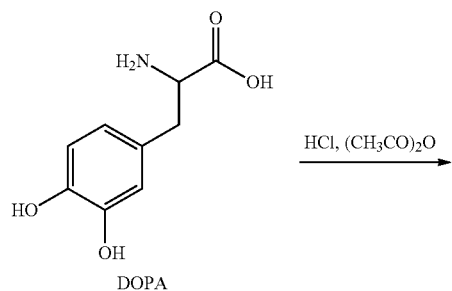

DOPA

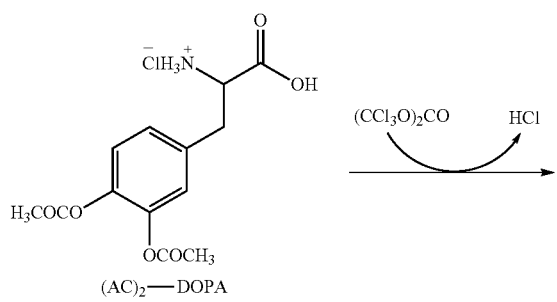

(AC)$_2$—DOPA

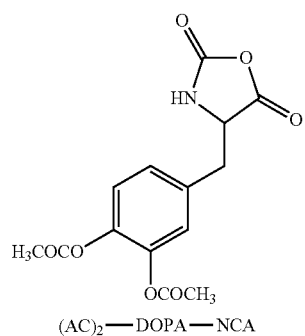

(AC)$_2$—DOPA—NCA

Preparation of a polyethyleneimine-graft-(polyethyleneglycol;poly-3,4-dihydroxyphenylalanine) in operation (c) may be executed by multi-initiation of the polyethyleneimine-graft-polyethyleneglycol formed in operation (a) and the 3,4-dihydroxyphynylalanine N-carboxyl anhydride (DOPA-NCA) synthesized in operation (b) in an organic solvent, enabling polymerization thereof. The poly DOPA in the copolymer is synthesized by inducing polymerization of 3,4-dihydroxyphynylalanine N-carboxyl anhydride (DOPA-NCA) using the primary amine present in the polyethyleneimine-graft-polyethyleneglycol as a multi-initiator. According to the foregoing processes, the synthesized poly-3,4-dihydroxyphenylalanine (PDOPA) is combined with the polyethyleneimine-graft-polyethyleneglycol resulting in a final product, that is, the polyethyleneimine-graft-(polyethyleneglycol;poly-3,4-dihydroxyphenylalanine).

In operation (c), by regulating an added amount of 3,4-dihydroxyphynylalanine N-carboxyl anhydride (DOPA-NCA) used as a bio-mimetic conjugate site, the copolymer of the present invention may have controlled bonding ability and hydrophobic property ('hydrophobicity'). Preferably, a relative molar ratio of the polyethyleneimine-graft-polyethyleneglycol to 3,4-dihydroxyphynylalanine N-carboxyl anhydride (DOPA-NCA) ranges from 1:1 to 1:50. If the molar ratio is out of the above range, problems of increasing hydrophobicity or decreasing the bonding ability of the mussel adhesive protein-mimetic copolymer may arise.

The organic solvent used in operation (c) may include at least one selected from dimethyl sulfoxide (DMSO), tetrahydrofuran (THF), and chloroform (ClCH$_3$).

After completing polymerization in operation (c), operation (d) which is a process for de-protection of a protective hydroxyl group of the poly-3,4-dihydroxyphenylalanine (PDOPA) may be further included. According to one embodiment of the present invention, after completing polymerization of the polyethyleneimine-graft-(polyethyleneglycol;poly-3,4-dihydroxyphenylalanine), the product is dispersed in dimethyl formamide (DMF). Thereafter, by adding a proper amount of piperidine thereto, a hydroxyl group of the DOPA protected with an acetyl group may be de-acetylated, in turn resulting in a polyethyleneimine-graft-(polyethyleneglycol;poly-3,4-dihydroxyphenylalanine) represented by the following structure:

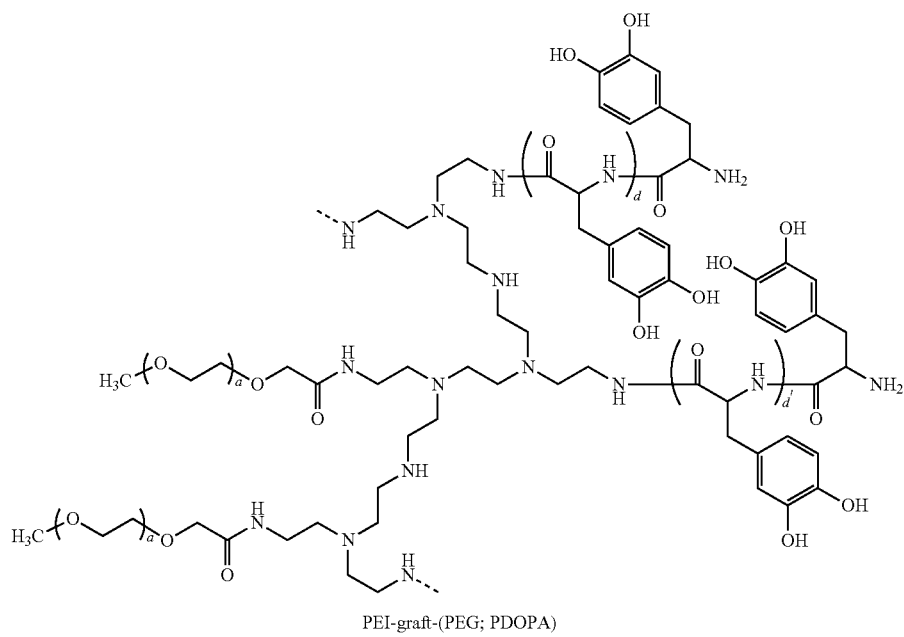

PEI-graft-(PEG; PDOPA)

[wherein a ranges from 2 to 1200, and d and d⊙ each independently ranges from 1 to 100.]

Polyethyleneimine-graft-(polyethyleneglycol;poly-3,4-dihydroxyphenylalanine) (PEI-graft-(PEG; PDOPA)

The polyethyleneimine-graft-(polyethyleneglycol;poly-3,4-dihydroxyphenylalanine) used in the present invention may be a biocompatible branch type dispersion stabilizer comprising a mussel adhesive protein-mimetic biocompatible polymer and containing poly-3,4-dihydroxyphenylalanine, and useful in dispersing and stabilizing nanoparticles in an aqueous medium.

Such nanoparticles may comprise metal, metal oxide, metal alloys, organic polymer and/or inorganic polymer, and have a size of 100 nm or less. More particularly, at least one selected from a group consisting of; iron oxide, cobalt ferrite ($CoFe_2O_4$), manganese ferrite ($MnFe_2O_4$), iron-platinum alloys (Fe—Pt alloy), cobalt-platinum alloys (Co—Pt alloy), cobalt (Co), cadmium selenide (CdSe), cadmium telluride (CdTe), cadmium selenide/zinc sulfide core/shell (CdSe/ZnS core/shell), cadmium selenide/zinc selenide core/shell (CdSe/ZnSe core/shell), cadmium selenide/cadmium sulfide core/shell (CdSe/CdS core/shell), cadmium telluride/zinc sulfide core/shell (CdTe/ZnS core/shell), cadmium telluride/zinc selenide core/shell (CdTe/ZnSe core/shell), cadmium telluride/cadmium sulfide core/shell (CdTe/CdS core/shell), cadmium telluride/cadmium selenide core/shell (CdTe/CdSe core/shell), zinc sulfide (ZnS), cadmium sulfide (CdS), indium arsenide (InAs), indium phosphide (InP), indium arsenide/indium phosphide core/shell (InAs/InP core/shell), indium arsenide/cadmium selenide core/shell (InAs/CdSe core/shell), indium arsenide/zinc sulfide core/shell (InAs/ZnS core/shell), indium arsenide/zinc selenide core/shell (InAs/ZnSe core/shell), indium phosphide/cadmium selenide core/shell (InP/CdSe core/shell), indium phosphide/zinc sulfide core/shell (InP/ZnS core/shell), indium phosphide/zinc selenide core/shell (InP/ZnSe core/shell), gold (Au), palladium (Pd), platinum (Pt), polystyrene and Teflon.

The iron oxide may include FeO, $Fe_3O_4$ (magnetite), $\alpha$-$Fe_2O_3$, $\beta$-$Fe_2O_3$, $\gamma$-$Fe_2O_3$ (maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot H_2O$, $5Fe_2O_3 \cdot H_2O$, $FeOOH \cdot 0.4H_2O$, $Fe_8O_8(OH)_6(SO) \cdot nH_2O$, $Fe_{16}O_{16}(OH \cdot SO_4)_{12-13} \cdot 10$-$12H_2O$, and so forth. More preferably, $Fe_3O_4$ (magnetite), $\gamma$-$Fe_2O_3$ (maghemite) or a mixture of $Fe_3O_4$ (magnetite) and $\gamma$-$Fe_2O_3$ (maghemite) is used.

A core diameter of iron oxide used in the present invention may range from 1 to 25 nm. The core diameter of iron oxide may be observed by a transmission electron microscopy (TEM). If the core diameter of iron oxide is less than 1 nm, MR T2 contrast effects are reduced. On the contrary, when the core diameter of iron oxide exceeds 25 nm, the compound shows ferrimagnetic property and cannot be use for MRI.

A hydrodynamic diameter of each of the iron oxide nanoparticles stabilized in an aqueous medium by the mussel adhesive protein-mimetic copolymer, polyethyleneimine-graft-(polyethyleneglycol;poly-3,4-dihydroxyphenylalanine), may range from 3 to 100 nm. The hydrodynamic diameter may be measured by dynamic light scattering (DLS) while dispersing the nanoparticles in water. When the hydrodynamic diameter is less than 3 nm, iron oxide nanoparticles introduced in vivo and being hydrophilic may be easily excreted out of the body before depositing on the lymph nodes. On the other hand, if the hydrodynamic diameter exceeds 100 nm, the iron oxide nanoparticles introduced in vivo and being hydrophilic may be removed too early by an immune system in vivo (macrophage, etc.), thus not or minimally depositing on the lymph nodes.

The lymph node contrast imaging method may utilize a variation or difference in strength of MRI signals generated from lymph nodes before and after administration of a contrast agent for lymph node imaging, which includes a colloidal solution prepared by modifying the surface of iron oxide particles using the mussel adhesive protein-mimetic copolymer described above and then dispersing the same in water. The variation in strength of MRI signals in the lymph node may be determined on the basis of changes in T2 signals.

In order to maximize contrast imaging effects in the MRI method, introduction of the contrast agent used in the present invention may be conducted by intravenous injection, oral administration, etc. Among these, the intravenous injection is more preferably used to maximize deposition of iron oxide on the lymph node.

Among various nanoparticles described above, in the case where iron oxide nanoparticles dispersed and stabilized by the foregoing mussel adhesive protein-mimetic copolymer are used for in vivo MRI contrast imaging, a T2 signal attenuation ratio in the lymph node is observed to be about 80% or more, thus presuming that the iron oxide nanoparticles are useful for diagnosis of a lymph node metastatic cancer.

Other features and aspects will be apparent from the following detailed description, the drawings, and the claims.

Advantageous Effects

The mussel adhesive protein-mimetic copolymer used in the present invention has poly-3,4-dihydroxyphenylalanine (PDOPA) formed through multi-initiative polymerization, in turn having at least one unit of DOPA per molecule, that is multiple interaction ligands (MIL) and exhibiting a high bonding strength to a hydrophilic surface. Since the above copolymer has a positive charge, it may impart additional electrostatic bonding force to the surface of nanoparticles having a negative charge. Moreover, since numerous polyethyleneglycol molecules having hydrophilic property are bonded to branches of a branch type polyethyleneimine, high aqueous dispersion stabilization may be achieved through hydrophilic property and stereoscopic effects. Accordingly, iron oxide nanoparticle colloids dispersed and stabilized in an aqueous medium by the mussel adhesive protein-mimetic copolymer, as described in the present invention, a contrast agent for contrast enhanced lymphography, which includes the foregoing copolymer, and a lymph node contrast imaging method, may accomplish excellent in vivo contrast imaging effects, thereby being useful for diagnosis of lymph node metastatic cancer.

DESCRIPTION OF DRAWINGS

FIG. 1 illustrates a chemical structure of a mussel adhesive protein-mimetic copolymer and stabilization of nanoparticles used in the present invention;

FIG. 13 illustrates experimental results of stabilities of iron oxide nanoparticles and iron oxide nanoparticle colloid modified by a mussel adhesive protein-mimetic copolymer, and dispersed and stabilized in water, along with various pH values and ionic concentrations, wherein the hydrodynamic diameter (HD) is measured using the DLS device, followed by comparison of measured results (MIL0 (♦), MIL1 (▲) and MIL2 (○)); In FIG. 14, parts marked in (+) indicate a lymph node evaluated to be metastatic cancer as the MRI scanning and parts marked in (−) indicate a lymph node examined to be normal as the MRI scanning.

MODE FOR INVENTION

Figure 2:
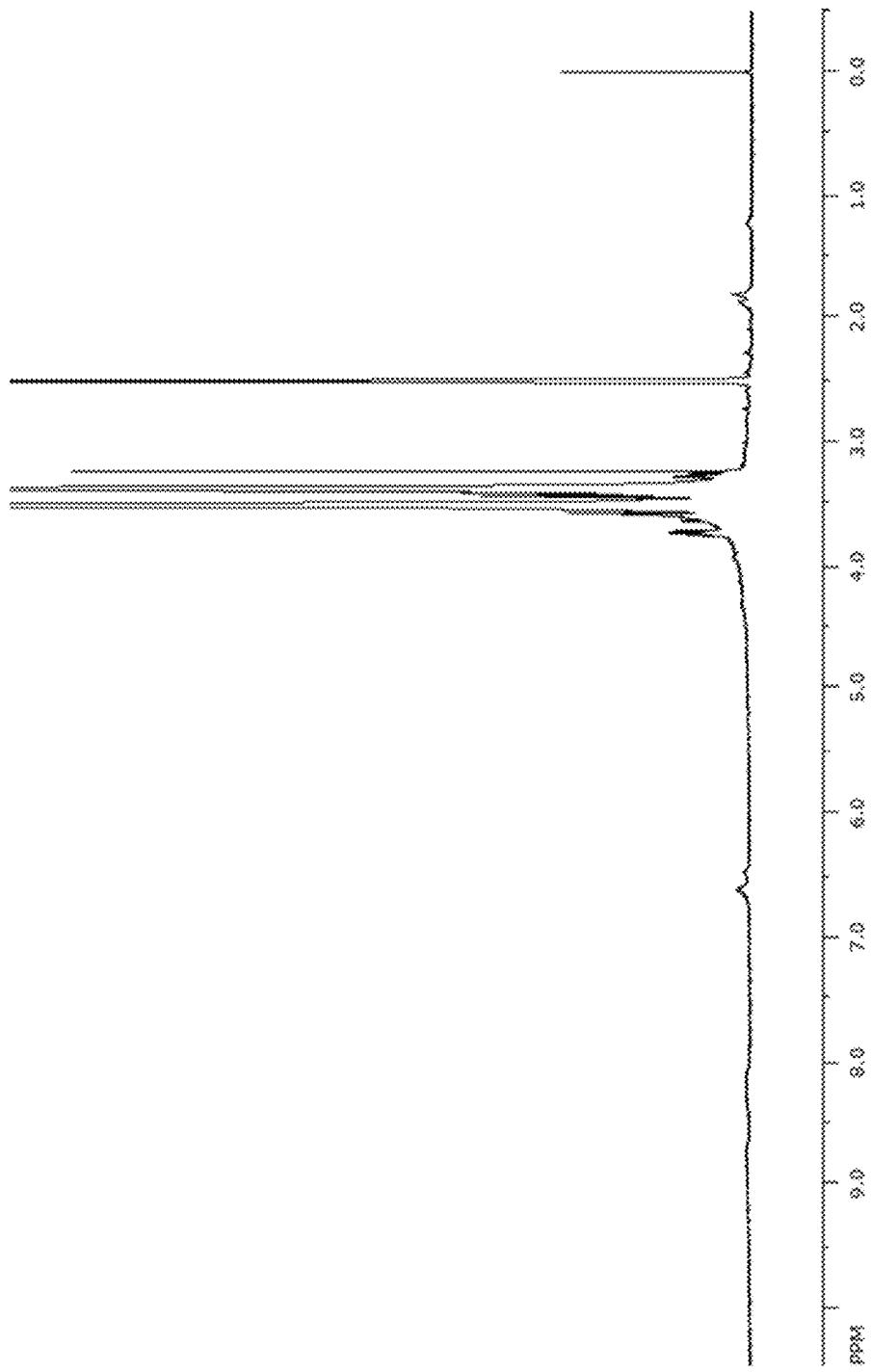
FIG. 2 illustrates analyzed results of $^1$H-NMR (in DMSO) of PEI-graft-(PEG;PDOPA$_5$) prepared in Preparative Example <1-6>.

The advantages, features and aspects of the present invention will become apparent from the following description of the embodiments with reference to the accompanying drawings, which is set forth hereinafter. However, such embodiments are provided to offer a clearer understanding of the present invention and the scope of technical configurations of the present invention should not be construed as limited the embodiments set forth herein. Rather, various modifications and/or alterations of principal concepts of the present invention and performance thereof may be easily made by those having ordinary knowledge in the related art.

Hereinafter, exemplary embodiments will be described in detail with reference to the accompanying drawings.

L-3,4-dihydroxy phenylalanine ('L-DOPA'), PEG-OH (5,000 Da), dimethyl formamide (DMF), N-hydroxy succinimide (NHS), N,N'-dicyclohexyl carbodiimide (DCC), acetic acid anhydride, glacial acetic acid, methylene chloride (MC) and chloroform were purchased from Sigma Chemical Company (St. Louis, Mo.), and PEI (1,800 Da (PEI 1,800)) was purchased from Alfa Aesar. For 48 hours before use, these materials were dried 40° C. under vacuum.

Preparative Example 1
Synthesis of Mussel Adhesive Protein-Mimetic Copolymer
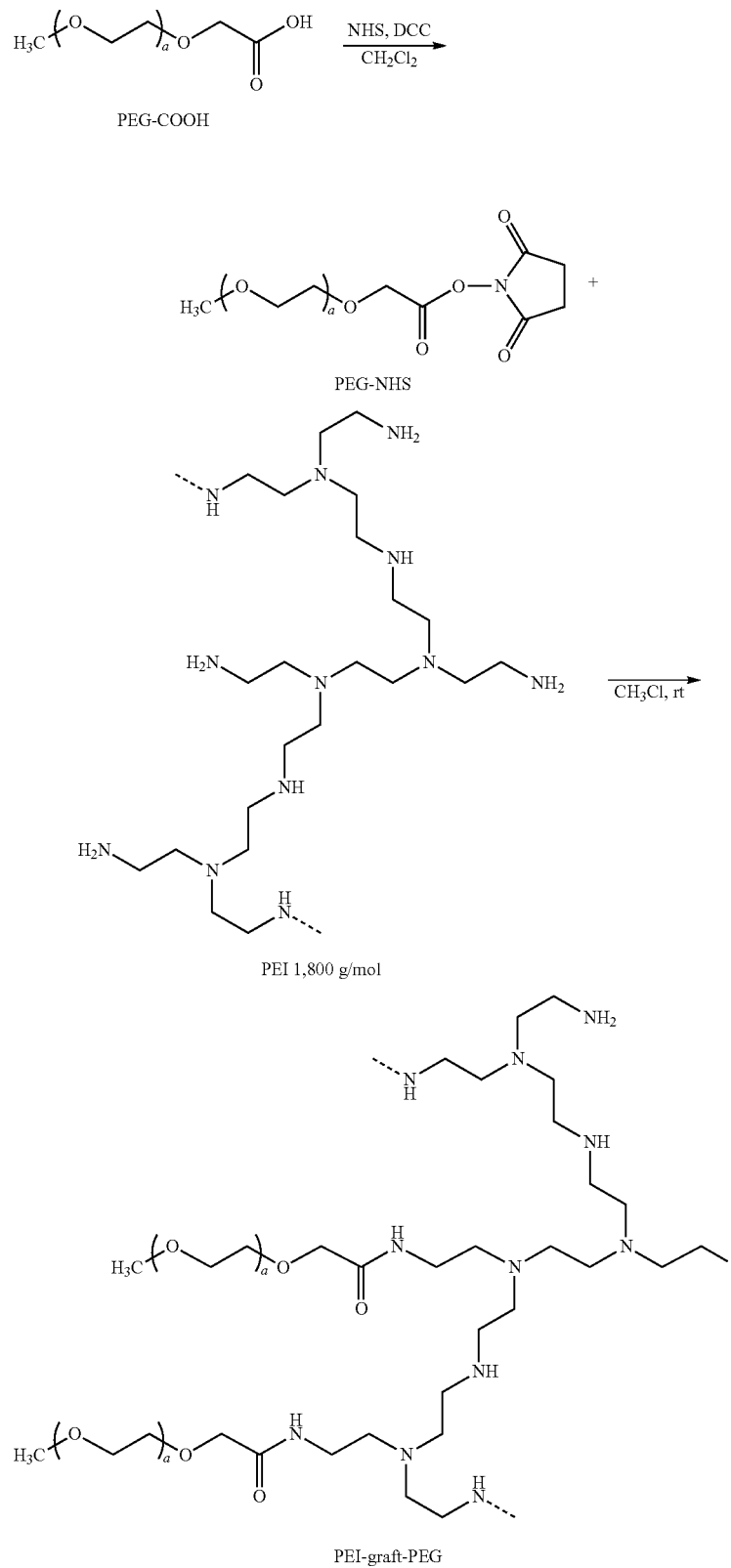

-continued
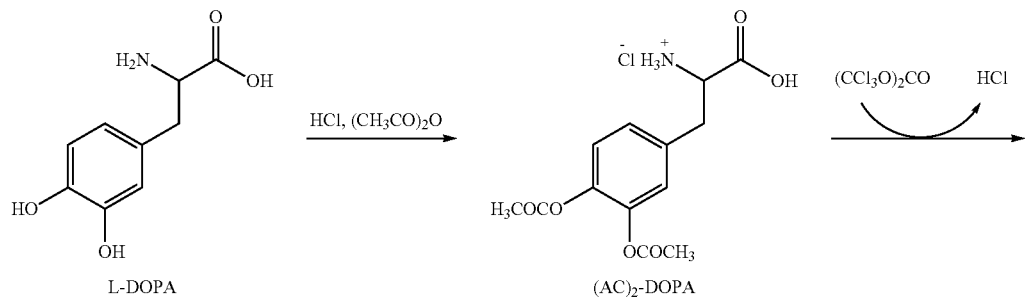
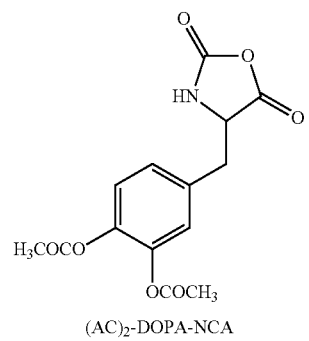
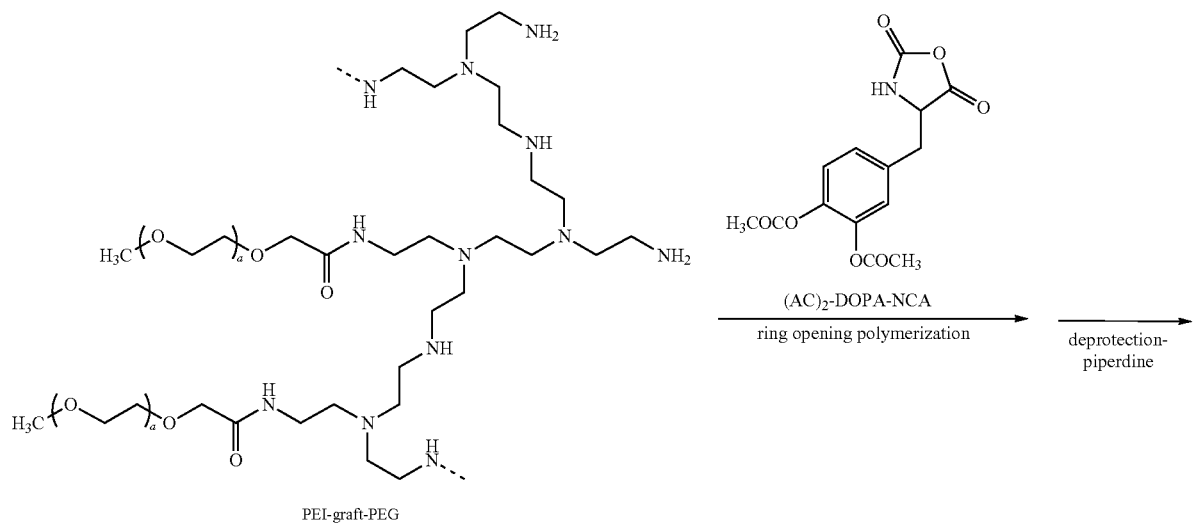

-continued

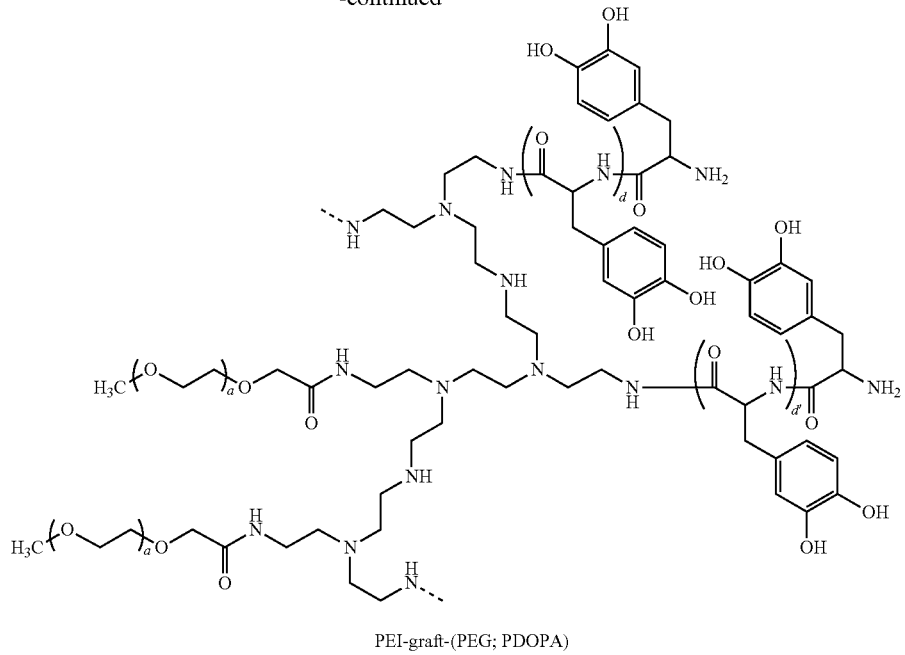

PEI-graft-(PEG; PDOPA)

<1-1> Activation of Polyethyleneglycol
<1-1-1> Use of Dicyclohexylcarbodiimide/N-Hydroxy Succinylimide (DCC/NHS)

After mounting a reflux condenser, methoxy polyethyleneglycol carboxyl (PEG-COOH, 5000) (10 g) was dissolved in methylene chloride ($CHCl_2$) (50 ml) in a 250 ml flask. Then, N-hydroxysuccinimide (NHS) (0.52 g) and dicyclohexylcarbodiimide (DCC) (0.74 g) were added thereto, followed by a reaction at room temperature for 20 hours. After removing dicyclohexylurea through filtration, this material was precipitated in diethylether, resulting in polyethyleneglycol in an activated state (PEG-NHS). (Yield=87%) $^1H$ NMR (300 MHz, $CDCl_3$): ⊚4.1 (b, —CO—$CH_2$—$CH_2$—$CH_2$—O—), 3.5-3.8 (m, —$CH_2CH_2O$—), 2.8 (b, —CO—$CH_2$—$CH_2$—CO—), 1.8 (b, —CO—$CH_2$—$CH_2$—$CH_2$—$CH_2$—$CH_2$—O—), 1.2 (b, —CO—$CH_2$—$CH_2$—$CH_2$—$CH_2$—$CH_2$—O—).

<1-1-2> Use of Hexamethylene Diisocyanate (HDMI)

After mounting a reflux condenser, methoxy polyethyleneglycol (PEG-OH) (15.23 g) was dissolved in chloroform ($CHCl_3$) (15 ml) in a 100 ml flask. Then, the solution was treated using hexamethylene diisocyanate (HMDI) (60 ml), followed by a reaction for 24 hours to prepare a polymer. After completing the reaction, the polymer was precipitated in petroleum ether to purify the same and, after washing with petroleum ether (400 ml) three times, the washed material was dissolved again in chloroform ($CHCl_3$) (20 ml). After then, the solution was precipitated again in petroleum ether (500 ml) to purify the same. The foregoing procedure was repeated 10 times, followed by drying under vacuum, resulting in polyethyleneglycol in an activated state (Yield=80%).

<1-2> Formation of a Polyethyleneimine-Graft-Polyethyleneglycol (PEI-Graft-PEG)

The activated polyethyleneglycol (PEG-NHS) (2 g) obtained in Example <1-1> was dissolved in chloroform (200 ml). Then, after dissolving polyethyleneimine (Alfa Aesar, 1800 Da, 0.5 g) in chloroform (50 ml), the polyethyleneglycol solution was added drop by drop thereto to conduct a covalent bonding reaction between polyethyleneglycol and polyethyleneimine. Here, the reaction was executed for 24 hours and, after completing the reaction, the resultant product was concentrated to reach a total volume of 30 ml by a vacuum concentrator. Following this, the concentrated material was precipitated in diethylether to obtain a polyethyleneimine-graft-polyethyleneglycol (PEI-graft-PEI). (Yield=85%)$^1H$ NMR (300 MHz, $D_2O$). As a result of measurement (—$CH_2CH_2O$— of PEG at 3.5-3.8 ppm and —$CH_2CH_2NH$— of PEI at 2.5-3.2 ppm), $M_n$ of PEI-graft-PEG was found to be about 41,800 Da. It was presumed that each PEI-graft-PEG has almost 8 (hereinafter, referred to as $PEI_1$-graft-$PEG_8$). $^1H$ NMR (300 MHz, $D_2O$): ⊚3.5-3.8 (m, —$CH_2CH_2O$—), 3.3 (s, $CH_3O$—), 2.5-3.2 (m, —$CH_2CH_2NH$—).

<1-3> Protection of Hydroxyl Group of DOPA Amino Acid

L-DOPA (3 g) was suspended in glacial acetic acid (100 ml), followed by purging dried gas of hydrochloric acid at room temperature for 5 hours. After adding acetic acid anhydride (3 ml) and reacting at room temperature for 1 hour 30 minutes, 3 ml of acetic acid anhydride was further added and a reaction was conducted in an oil bath at 60° C. for 30 minutes. The reaction product was concentrated in a vacuum concentrator and unreacted acetic acid anhydride was removed by adding ethanol. Thereafter, the remaining product was precipitated in diethylether to obtain DOPA amino acid having a protected hydroxyl group ($DOPA(Ac)_2$). (Yield=80%)$^1H$ NMR (300 MHz, $D_2O$): ⊚6.7-6.9 (m, —$C_6H_3(OH)_2$), 4.0 (m, $C_6H_3(OH)_2$—$CH_2$—CH(N—)—C(O)N—), 3.2 (m, $C_6H_3(OH)_2$—$CH_2$—CH—), 2.4 (s, $CH_3$(CO)—).

<1-4> Synthesis of DOPA Amino Acid N-Carboxyl Anhydride (DOPA-NCA)

0.5 g of the DOPA amino acid having a protected hydroxyl group synthesized in Example <1-3> as well as 0.5 g of triphosgene were dispersed in THF (50 ml) and reacted in an oil bath at 60° C. Next, the reaction product was precipitated in hexane (800 ml), dissolved in THF (50 ml) and precipitated again in hexane. The foregoing procedure was repeated three times. After purifying, the product was dried using a vacuum dryer, resulting in DOPA N-carboxyl anhydride (DOPA ($AC_2$)—NCA). (Yield=65%) $^1$H NMR (300 MHz, DMSO): ⊚6.2-6.9 (m, —$C_6H_3(OH)_2$), 4.3 (t, —NHCHCO—), 3.7 (m, $C_6H_3(OH)_2$—$CH_2$—CH(N—)—C(O)N—), 3.3 (m, $C_6H_3(OH)_2$—$CH_2$—CH—), 2.4 (s, $CH_3(CO)$—).

<1-5> Synthesis of Polyethyleneimine-Graft-(Polyethyleneglycol;Poly-3,4-Dihydroxyphenylalanine) (PEI-Graft-(PEG;PDOPA))

0.5 g of the polyethyleneimine-graft-polyethyleneglycol (PEI-graft-PEG) prepared in Example <1-2> and the DOPA N-carboxyl anhydride (DOPA($AC_2$)-NCA) prepared in Example <1-4> were used in different molar ratios (1:5 and 1:15, respectively) and reacted in THF solvent, thus synthesizing a polyethyleneimine-graft-(polyethyleneglycol;poly-3,4-dihydroxyphenylalanine) (Yield, molar ratio 1:5=85%, molar ratio 1:15=87%).

<1-6> De-Protection of Polyethyleneimine-Graft-(Polyethyleneglycol;Poly-3,4-Dihydroxyphenylalanine)

Figure 3:
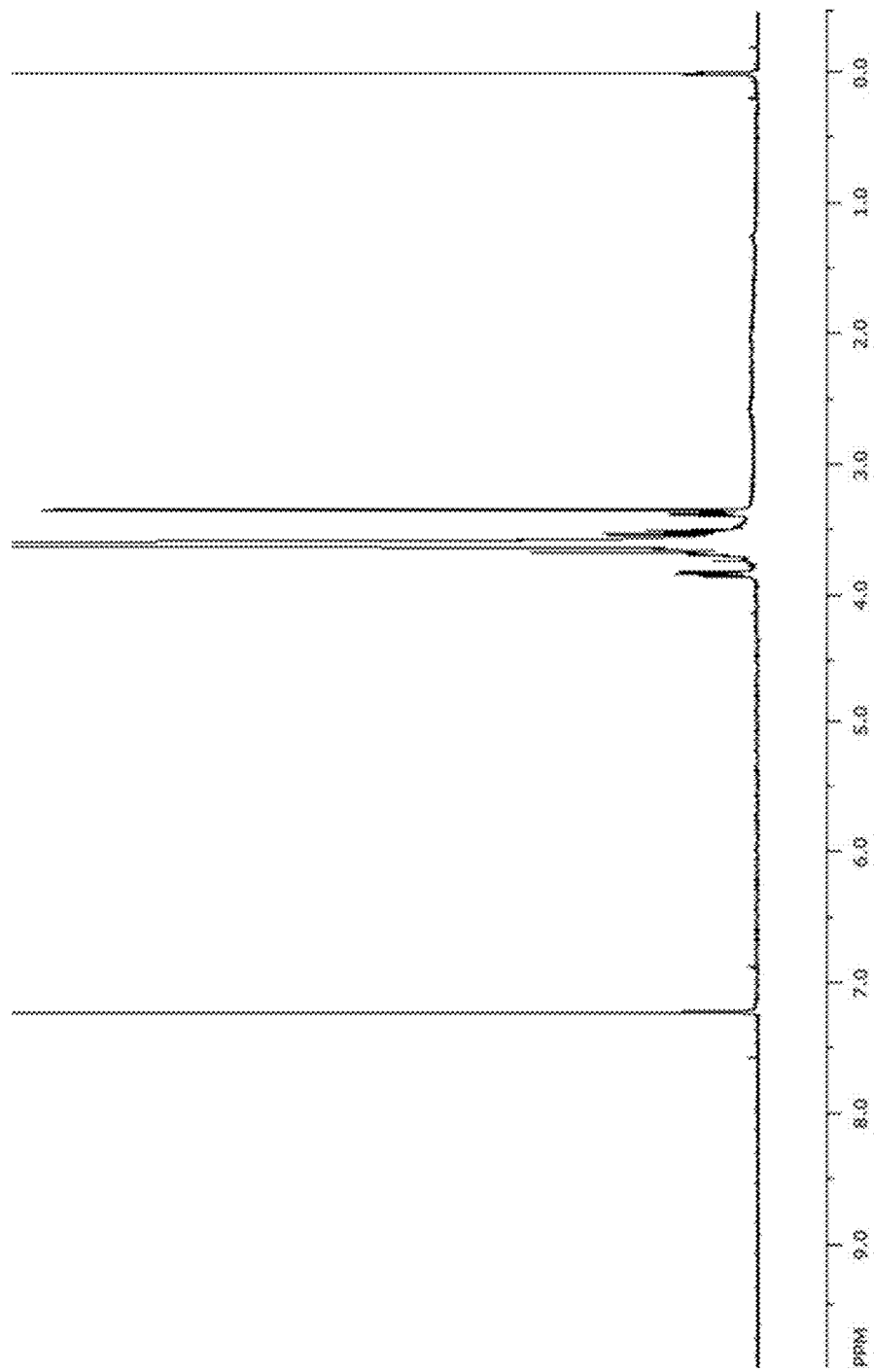
FIG. 3 illustrates analyzed results of $^1$H-NMR (in CDCl$_3$) of PEI-graft-(PEG;PDOPA$_5$) prepared in Preparative Example <1-6>.
Figure 4:
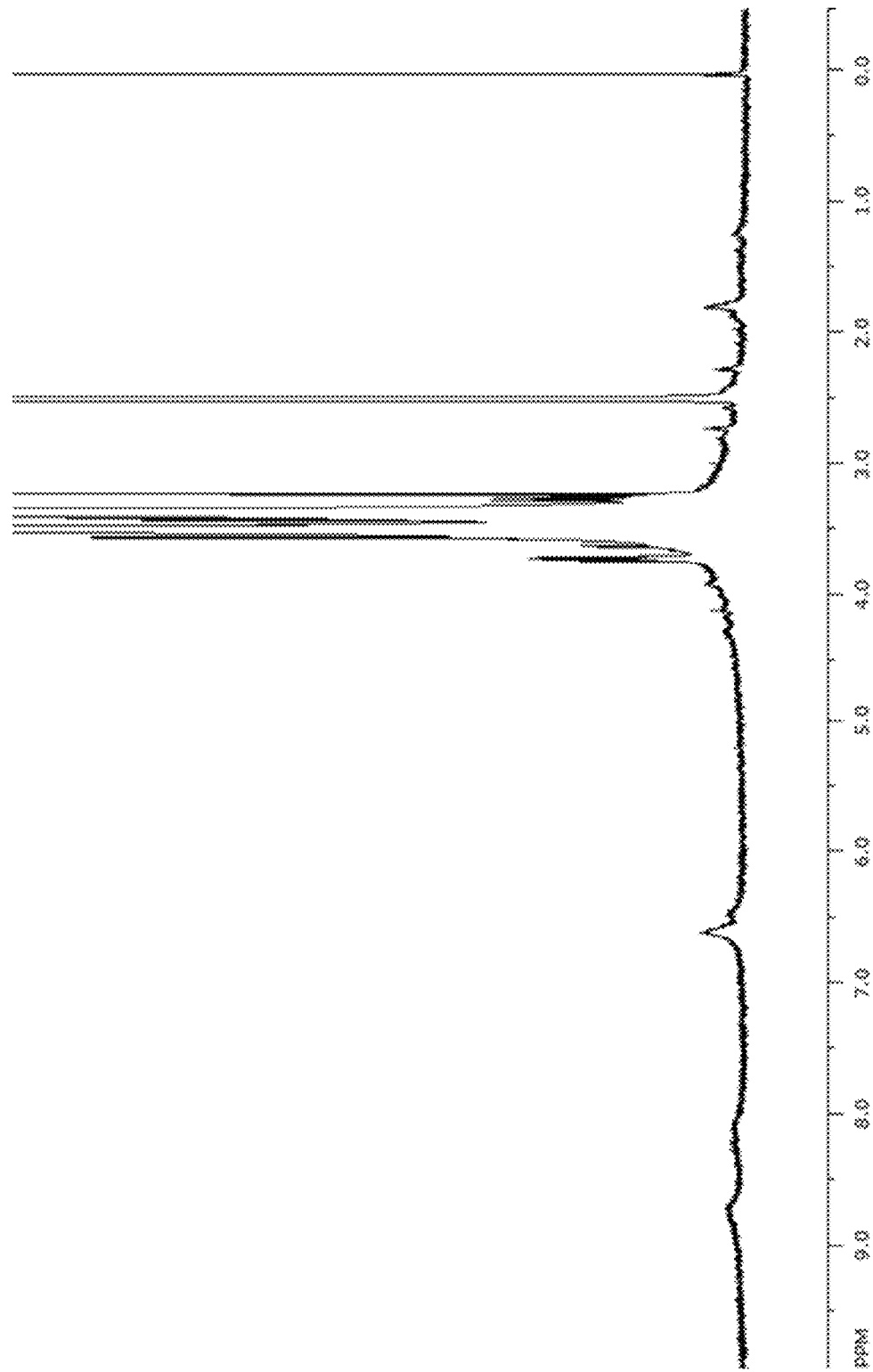
FIG. 4 illustrates analyzed results of $^1$H-NMR (in DMSO) of PEI-graft-(PEG;PDOPA$_{15}$) prepared in Preparative Example <1-6>.
Figure 5:
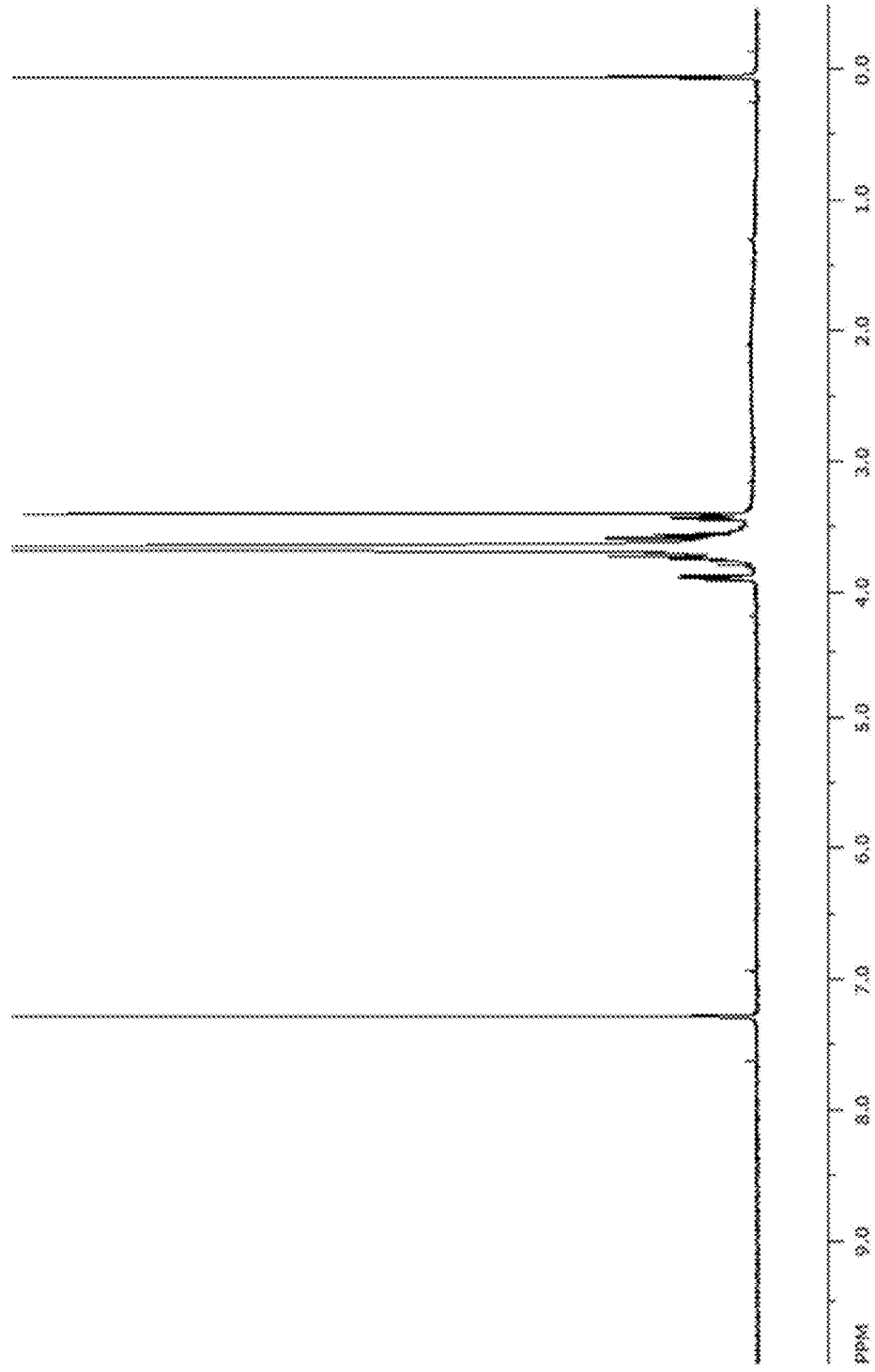
FIG. 5 illustrates analyzed results of $^1$H-NMR (in CDCl$_3$) of PEI-graft-(PEG;PDOPA$_{15}$) prepared in Preparative Example <1-6>.

After dissolving 0.5 g of the polyethyleneimine-graft-(polyethyleneglycol;poly-3,4-dihydroxyphenylalanine) synthesized in Example <1-5> in DMF (30 ml), 8 ml of piperidine was added thereto. 15 minutes after reaction, the reaction product was precipitated in diethylether to obtain a polyethyleneimine-graft-(polyethyleneglycol;poly-3,4-dihydroxyphenylalanine) in which a protective hydroxyl group of DOPA is de-protected. (Yield, molar ratio 1:5=80% [FIGS. 2 and 3], molar ratio 1:15=81% [FIGS. 4 and 5]). The following Table 1 shows assayed results of a structure of the mussel adhesive protein-mimetic copolymer of the present invention and characteristics thereof, wherein the structure of a polymeric copolymer and characteristics thereof have been assayed through $^1$H-NMR and UV-Vis spectroscopy and using a fluorescent label.

Preparative Example 2

Preparation of Iron Oxide ($Fe_3O_4$) Nanoparticles Stabilized by Mussel Adhesive Protein-Mimetic Copolymer 10 mg of iron oxide nanoparticles ($Fe_3O_4$) which were synthesized in an organic solvent and stabilized with oleic acid, as well as 60 mg of mussel adhesive protein-mimetic copolymers (MIL1 and MIL2, respectively), were dispersed in 10 ml of chloroform ($CHCl_3$) and agitated at room temperature for 30 minutes. After evaporating chloroform ($CHCl_3$) and adding distilled water to the residue, the dispersed product was filtrated through a 200 nm syringe filter (MCE syringe filter, Fisher Scientific). After centrifuging to remove unreacted stabilizer, filtration was repeated 3 to 5 times using a spin filter (Millipore, 10K NMWL, 10000×g, 10 min). The resultant product was dispersed in an aqueous system having pH 7 (0.01M PBS: Phosphate Buffered Saline solution).

Example 1

Cell Viability Test in Colloidal Solution of Iron Oxide ($Fe_3O_4$) Nanoparticle Stabilized by Mussel Adhesive Protein-Mimetic Copolymer The iron oxide ($Fe_3O_4$) stabilized using the mussel adhesive protein-mimetic copolymer, which has physical properties shown in the following Table 2, according to the methods proposed in Preparative Examples 1 and 2, was dispersed in water to prepare a colloidal solution.

TABLE 1

Analysis of structure and characteristics of mussel adhesive protein-mimetic copolymer

| Name of sample | Copolymer | Number average molecular weight | | Molar ratio along with individual materials | | | $M_n{}^a$ | CMC $(g/L)^b$ |
| | | PEG $M_n$ | PEI $M_n$ | PEG | PEI | DOPA | | |
|---|---|---|---|---|---|---|---|---|
| MIL0 copolymer | PEI-graft-PEG | 5,000 | 1,800 | 8 | 1 | — | 41,800 | — |
| MIL1 copolymer | PEI-graft-(PEG; PDOPA) | 5,000 | 1,800 | 8 | 1 | 5 | 42,800 | 0.015 |
| MIL2 copolymer | PEI-graft-(PEG; PDOPA) | 5,000 | 1,800 | 8 | 1 | 15 | 44,800 | 0.005 |

$^a M_n$: number average molecular weight, which is assayed using $^1$H-NMR and UV-Vis spectra
$^b$CMC: Critical Micelle Concentration, which is assayed using a fluorescent label (Hoechst 33342)

TABLE 2

Colloidal solution of iron oxide ($Fe_3O_4$) stabilized using mussel adhesive protein-mimetic copolymer

| Name of sample | Diameter of iron oxide nanoparticle (nm)[1] | Number average molecular weight | | Molar ratio | | | Hydrodynamic diameter (nm)[2] |
|---|---|---|---|---|---|---|---|
| | | PEG $M_n$ | PEG $M_n$ | PEG | PEI | DOPA | |
| PD1 colloidal solution | 10 | 5000 | 1800 | 7 | 1 | 20 | 30 |
| PD2 colloidal solution | 10 | 2000 | 1800 | 6 | 1 | 20 | 16 |

[1] Diameter of iron oxide nanoparticle: a diameter of iron oxide particle only excluding a dispersion stabilizing material, which is measured by Transmission Electron Microscopy (TEM)
[2] Hydrodynamic diameter: a diameter of a material dispersed in water and containing a dispersion stabilizing material, which is a number average diameter measured in a dispersed state in an aqueous system by a dynamic light scattering (DLS) device (Malvern Co., Zetasizer NanoZS)

To the dispersed and stabilized iron oxide ($Fe_3O_4$) nanoparticles shown in Table 2, PBS powder was added to reach a concentration of 0.01M. In order to identify bio-applicability, MTT assay was executed with Hep G2 cells.

respectively. Moreover, Sample 10 was 100% medium with neither PD1 nor PD2. As controls, PBS solutions were prepared for PD1 and PD2, respectively, according to the foregoing procedures (see TABLE 3).

TABLE 3

Iron oxide ($Fe_3O_4$) nanoparticles colloid sample for cell viability test

| | PD1 colloid | | PD2 colloid | | Control |
|---|---|---|---|---|---|
| No. | Sample + medium | Iron content (ppm) | Sample + medium | Iron content (ppm) | Sample + medium |
| | Crude solution | 1680 | Crude solution | 1320 | Crude solution (0.01M PBS solution) |
| 0 | Crude solution, 350 μL + medium 350 μL | 840 | Crude solution, 350 μL + medium 350 μL | 660 | Crude solution, 350 μL + medium 350 μL |
| 1 | No. 0, 200 μL + medium 200 μL | 420 | No. 0, 200 μL + medium 200 μL | 330 | No. 0, 200 μL + medium 200 μL |
| 2 | No. 1, 200 μL + medium 200 μL | 210 | No. 1, 200 μL + medium 200 μL | 165 | No. 1, 200 μL + medium 200 μL |
| 3 | No. 2, 200 μL + medium 200 μL | 105 | No. 2, 200 μL + medium 200 μL | 82.5 | No. 2, 200 μL + medium 200 μL |
| 4 | No. 3, 200 μL + medium 200 μL | 52.5 | No. 3, 200 μL + medium 200 μL | 41.25 | No. 3, 200 μL + medium 200 μL |
| 5 | No. 4, 200 μL + medium 200 μL | 26.25 | No. 4, 200 μL + medium 200 μL | 20.63 | No. 4, 200 μL + medium 200 μL |
| 6 | No. 5, 200 μL + medium 200 μL | 13.13 | No. 5, 200 μL + medium 200 μL | 10.31 | No. 5, 200 μL + medium 200 μL |
| 7 | No. 6, 200 μL + medium 200 μL | 6.56 | No. 6, 200 μL + medium 200 μL | 5.16 | No. 6, 200 μL + medium 200 μL |
| 8 | No. 7, 200 μL + medium 200 μL | 3.28 | No. 7, 200 μL + medium 200 μL | 2.58 | No. 7, 200 μL + medium 200 μL |
| 9 | No. 8, 200 L + medium 200 μL | 1.64 | No. 8, 200 μL + medium 200 μL | 1.29 | No. 8, 200 μL + medium 200 μL |
| 10 | Medium 400 μL | 0 | Medium 400 μL | 0 | Medium 400 μL |

<1-1> Preparation of Sample

After passing PD1 and PD2 containing PBS through a 0.2 μm sterile syringe filter, respectively, a concentration was determined using a inductively coupled plasma-atomic emission spectroscopy (ICP-AES). The PD1 and PD2 were taken with an aliquot by 200 μL, respectively, and the aliquot was mixed with 200 μL of a medium (DMEM: Dulbeco's Modified Eagles's Medium 89%, Pluronic F-127 10%, AA: antibiotic-antimycotic 1%) to prepare Sample 0. 350 μL of the sample 0 was mixed with 350 μL of a medium to prepare Sample 1. Also, 350 μL of Sample 1 was mixed with 350 μL of the medium to prepare another sample named Sample 2. As such, the initial concentration was diluted to ½ thereof to prepare nine (9) samples from 1 to 9 for PD1 and PD2, <1-2> Culturing and Preparation of Cell (HepG2)

After proliferating HepG2 cells through subculture, the cells were charged in 96-well plate to obtain 100,000 cells/well. Here, among these 96 wells, only 60 wells were used except those in periphery of the plate. In order to fix HepG2 cells on the bottom of the well plate, these were incubated at 37° C. for 24 hours.

<1-3> Addition of Sample

The medium was removed from the well plate in which HepG2 prepared in <1-2> was incubated. Each well of the well plate free from the medium, was charged with 100 μL of each of respective samples 1 to 10 of PD1, PD2 and controls, respectively, which were prepared in <1-1> shown in Table 3. Here, each of the samples and controls was prepared in three (3) folds. After charging the sample, incubation was executed at 37° C. for 24 hours.

<1-4> Cell Viability Test (MTT Test)

MTT test is an experimentation to determine cell viability using a principle wherein a yellow MTT reagent based on tetrazolium salt is altered into violet formazan crystals by metabolically activated cells.

The MTT (3-(4,5-dimethylthiazol-2-yl)-2,5-diphenyl-2H-tetrazolium bromide) reagent used in the cell viability test was dissolved in a water bath at 37° C., 1 hour before the test. To each well of the 96-well plate into which the samples and controls prepared in <1-3> were introduced, 20 µL of the prepared MTT reagent was added. Here, special precaution is needed to prevent the test well from being exposed to light. In order to identify the metabolically activated cells, the test well was incubated at 37° C. for 4 hours after addition of the MTT reagent. After incubation, in order to dissolve violet formazan crystals, 100 µL of a soluble solution was added to each well and incubation was continued at 37° C. for 24 hours.

After incubation, optical densities at 550 nm and 690 nm, respectively, were measured using a microplate reader (Molecular Devices Co., Spectra Max 190) and cell viability was calculated from the measured optical densities. The cell viability may be calculated according to the following Equation 1.

$$\text{cell viability (\%)} = \frac{OD_{i,550} - OD_{i,690}}{ODS_{i,550} - ODS_{i,690}} \times 100 \quad \text{[Equation 1]}$$

$OD_{i,550}$: Optical density at 550 nm of well plate No. i in which the sample is introduced.

$OD_{i,690}$: Optical density at 690 nm of well plate No. i in which the sample is introduced.

$ODS_{i,550}$: Optical density at 550 nm of control well plate No. i.

$ODS_{i,690}$: Optical density at 690 nm of control well plate No. i.

Figure 6:
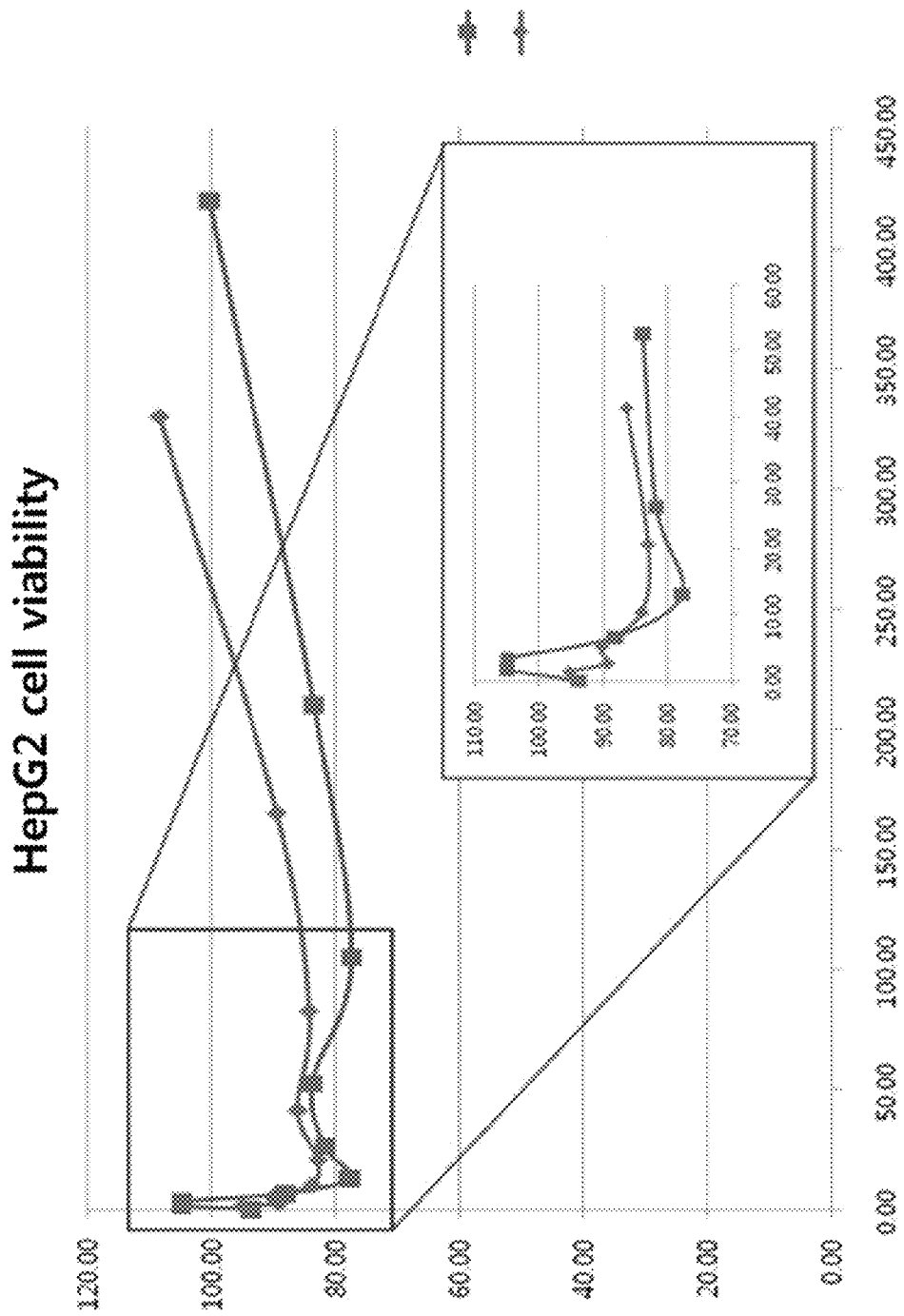
FIG. 6 illustrates viability of Hep G2 cells along with iron content of a colloidal solution in Example 1.
Figure 7:
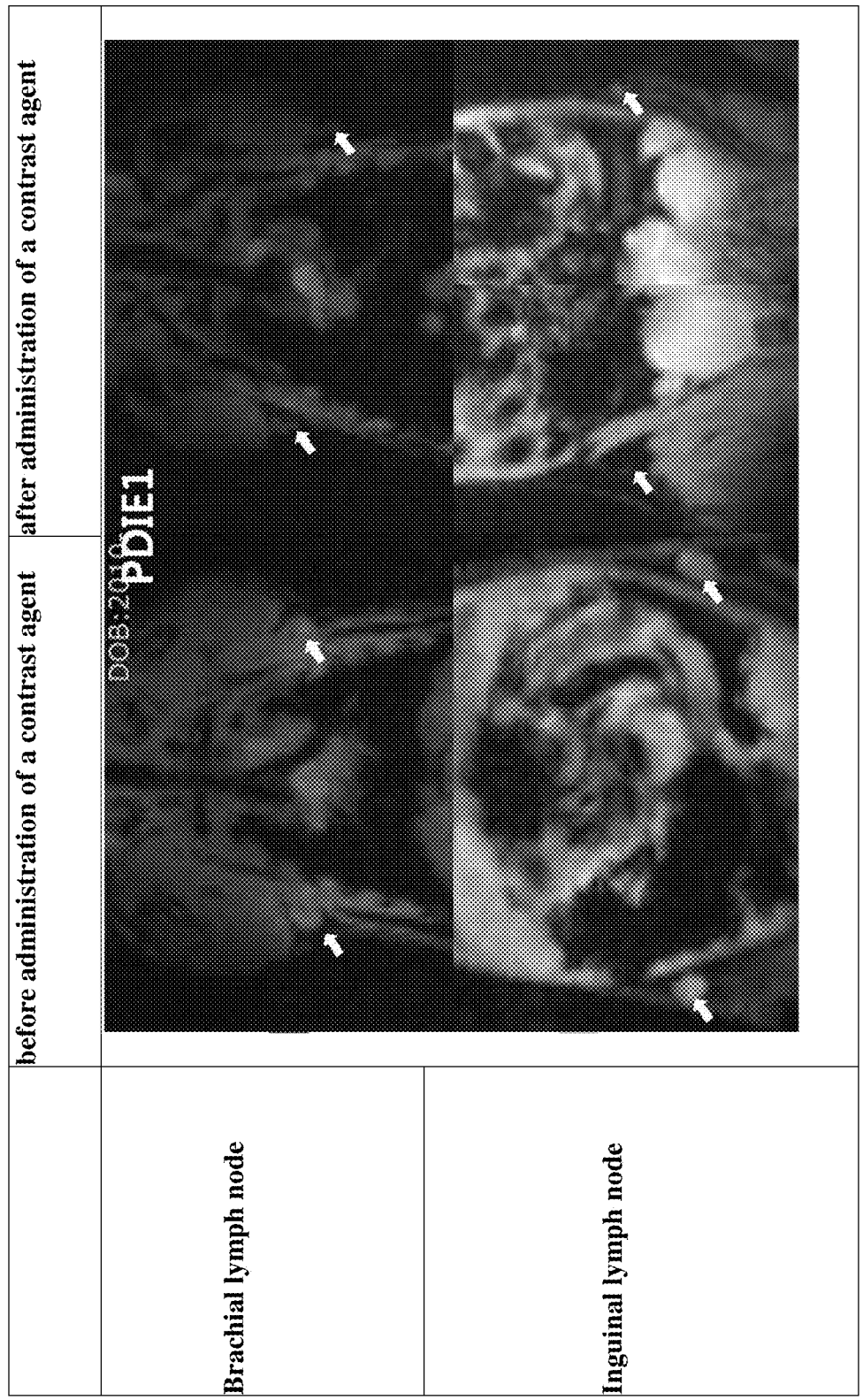
FIG. 7 is an image showing measured results of T2 signals in a nude mouse before and after administration of a contrast agent (PDIE1) in Example 2.
Figure 8:
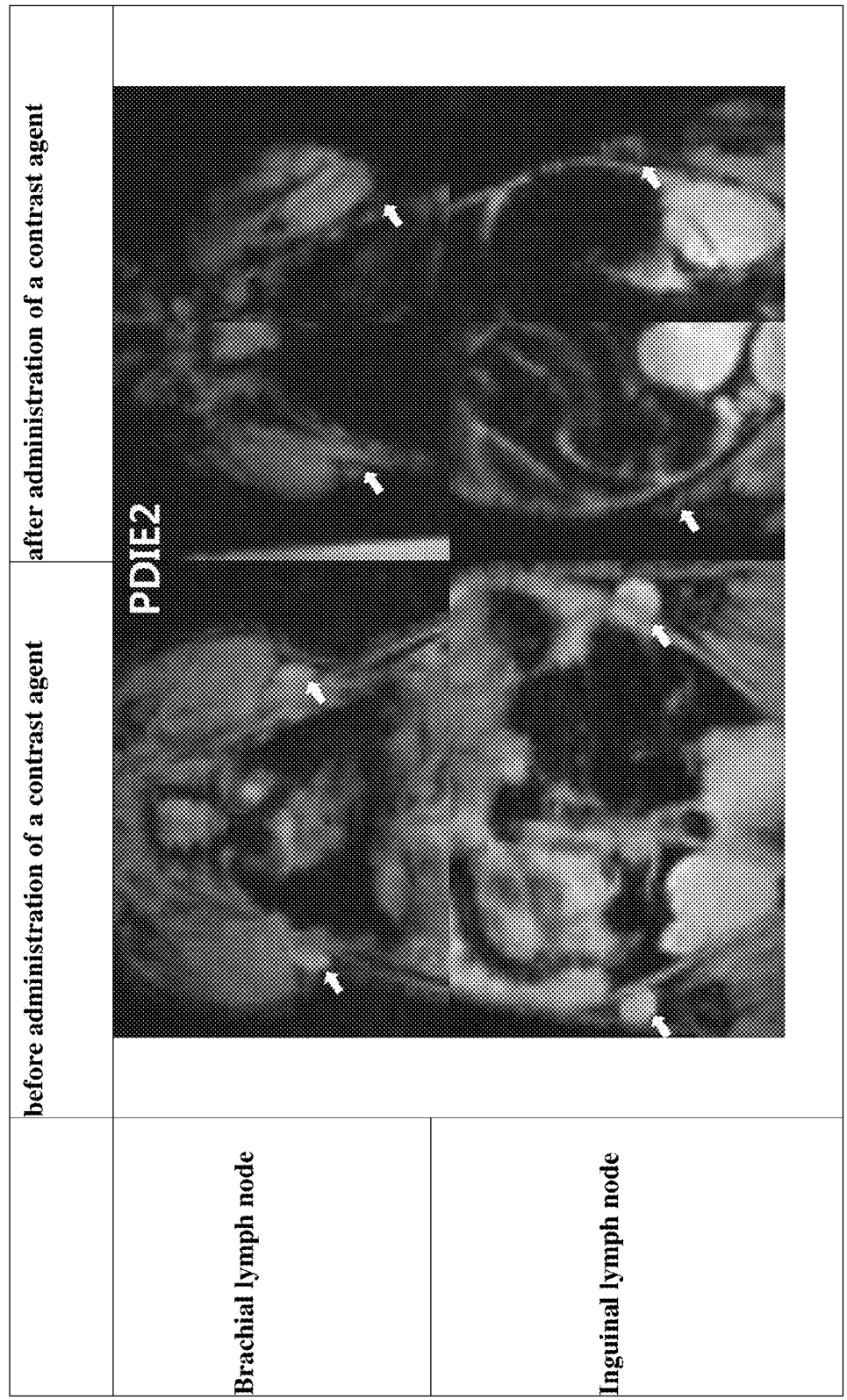
FIG. 8 is an image showing measured results of T2 signals in a nude mouse before and after administration of another contrast agent (PDIE2) in Example 2.
Figure 9:
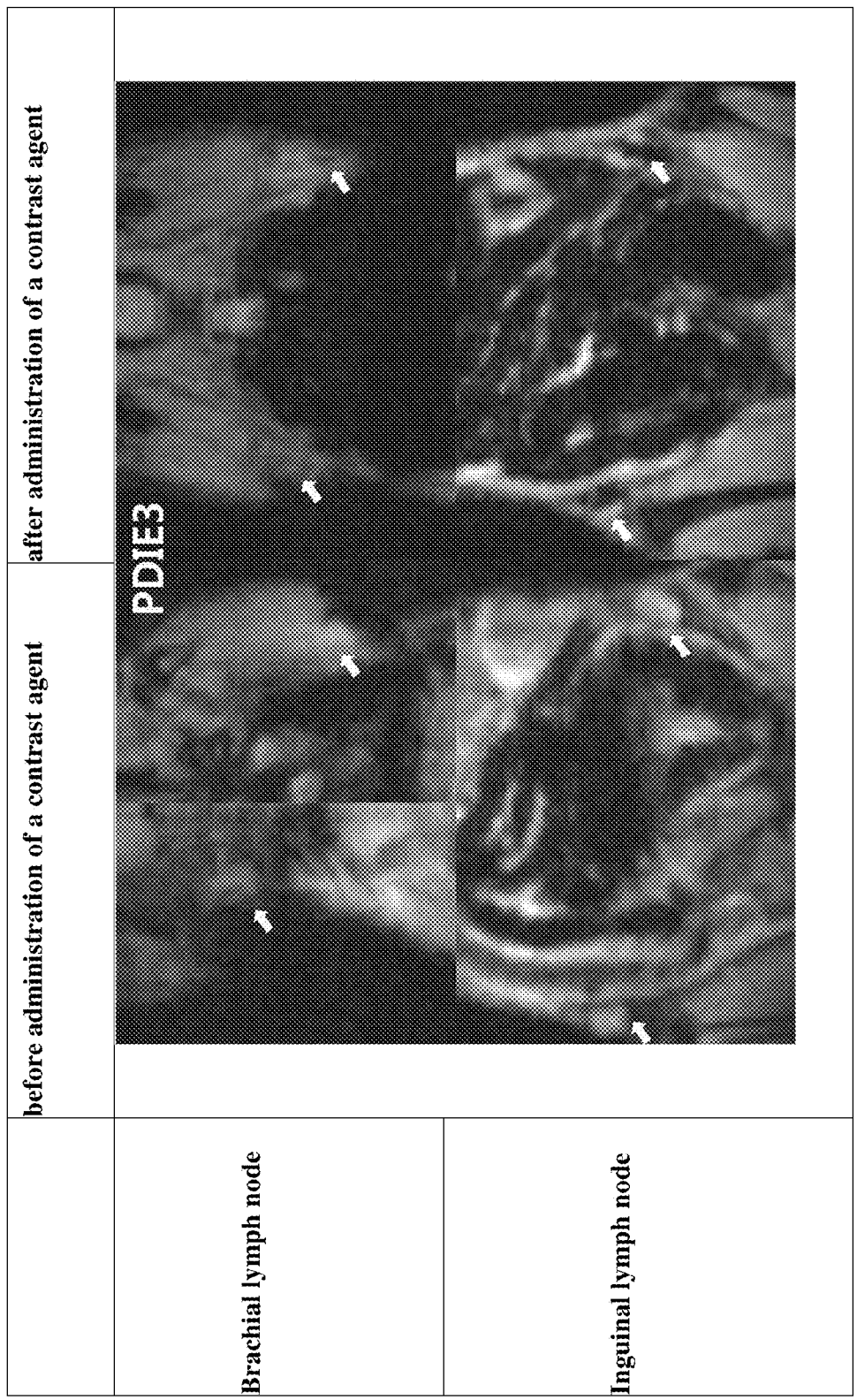
FIG. 9 is an image showing measured results of T2 signals in a nude mouse before and after administration of another contrast agent (PDIE3) in Example 2.
Figure 10:
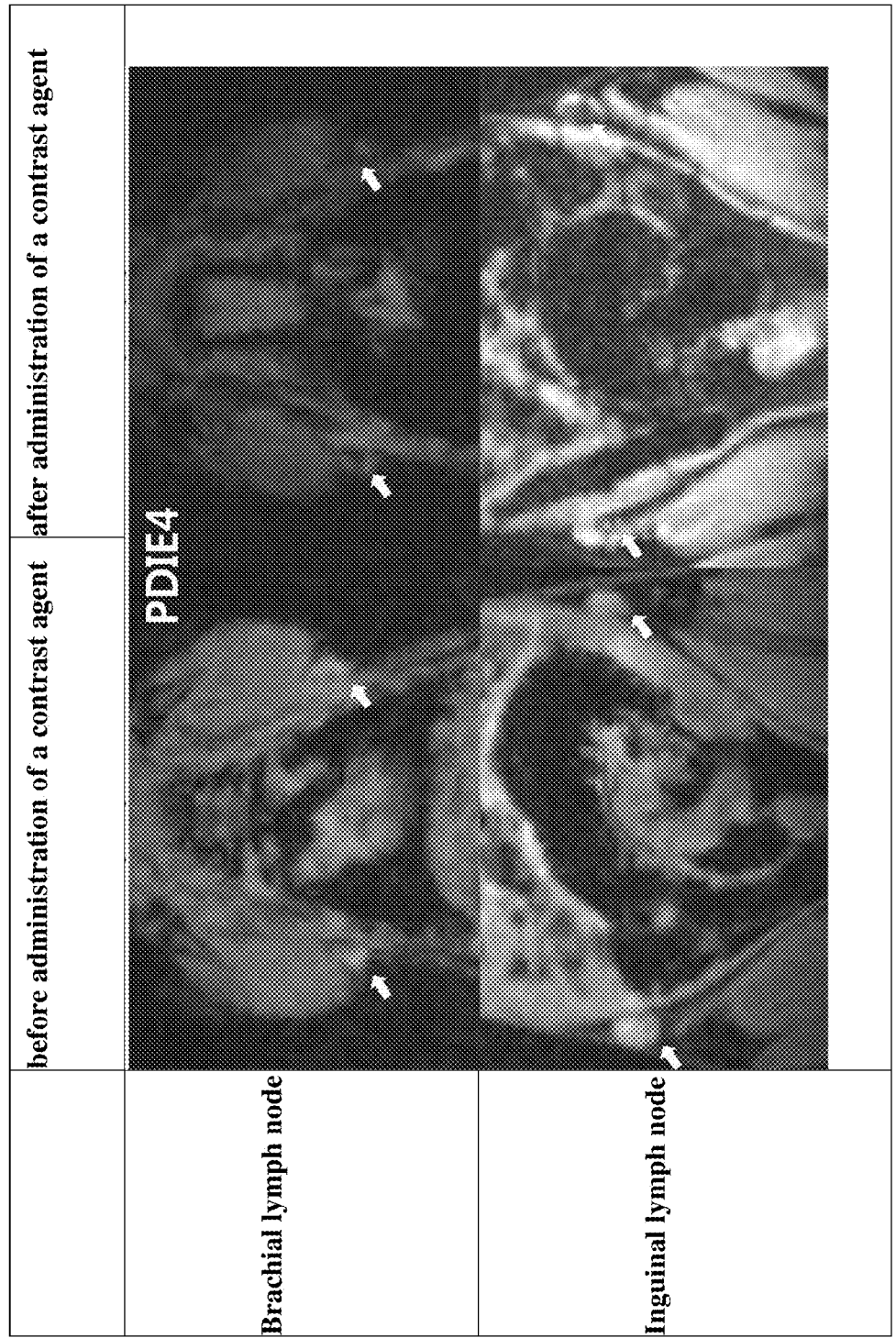
FIG. 10 is an image showing measured results of T2 signals in a nude mouse before and after administration of another contrast agent (PDIE4) in Example 2.

FIG. 6 is graphs illustrating results of cell viability test. In cell viability test, an acceptable error range (commonly, tolerance) is generally ±20%. From results of the present test, it can be found that 80% or more of cell viability was exhibited in the most part of a concentration section to be tested. Such results demonstrated that the iron oxide ($Fe_3O_4$) nanoparticles stabilized by the mussel adhesive protein-mimetic copolymer have no cellular toxicity and may be safely used in vivo.

Example 2

Determination of In Vivo MRI Performance of a Contrast Agent that Includes a Colloidal Solution Containing Iron Oxide ($Fe_3O_4$) Nanoparticles Stabilized by Mussel Adhesive Protein-Mimetic Copolymer The colloidal solutions containing iron oxide ($Fe_3O_4$) nanoparticles stabilized using the mussel adhesive protein-mimetic copolymers were prepared according to the method in Example 1.

TABLE 4

Iron oxide ($Fe_3O_4$) nanoparticle colloidal solution stabilized by mussel adhesive protein-mimetic copolymer for example 2

| Name of sample | Diameter of iron oxide nanoparticle (nm) | Number average molecular weight PEG $M_n$ | Number average molecular weight PEG $M_n$ | Molar ratio PEG | Molar ratio PEI | Molar ratio DOPA | Hydrodynamic diameter (nm) | Dose of administration (mg Fe/kg mouse) |
|---|---|---|---|---|---|---|---|---|
| PDIE1 colloidal solution | 10 | 2000 | 1800 | 8 | 1 | 15 | 26 | 10.4 |
| PDIE2 colloidal solution | 10 | 5000 | 1800 | 4 | 1 | 15 | 51 | 5.2 |
| PDIE3 colloidal solution | 20 | 5000 | 1800 | 8 | 1 | 20 | 48 | 5.2 |
| PDIE4 colloidal solution | 10 | 5000 | 1800 | 7 | 1 | 20 | 38 | 10.4 |

Adding a phosphate buffered saline (PBS) to each of the colloidal solutions, wherein iron oxide (Fe3O4) nanoparticles are dispersed and stabilized therein, as shown in Table 4, a contrast agent was prepared. In order to evaluate usability of the prepared contrast agent as an MRI contrast agent, a loop coil was used in an MRI diagnosis device (Trio 3.0T, Simens) to assay in vivo T2 contrast imaging performance.

Evaluation of in vivo contrast imaging performance was executed with nude mouse (Balb/nude). The nude mouse weighed 30 g. After anesthetizing, the mouse was horizontally placed in the MRI diagnosis device and observed along a cross-section thereof. MRI images of the nude mouse were subjected to measurement before and 24 hours after injecting the contrast agent, and lymph nodes before and after injecting the contrast agent were observed and compared to each other. PBS powder was added to the colloidal solution to reach a concentration of 0.01 M, to prepare a desired contrast agent. Iron content was analyzed through ICP-AES and an administration dose was calculated (Table 4) in consideration of the weight of the mouse, to prepare a contrast agent with a total volume of 500 µL. The contrast agent was injected through a tail vein of the mouse.

In vivo T2 imaging performance was determined using T2Me3d pulse sequence provided by Siemens Co. and particular parameters are as follows.

TR (repetition time)=40.0 msec, TE (echo time)=22.0 msec, FOV=49 mm×70 mm, Matrix size=256×180, slice thickness=0.6 mm, number of acquisition=6

FIGS. 7 to 10 partially illustrate in vivo MRI images obtained under the foregoing conditions.

In order to quantify T2 attenuation effects of the prepared contrast agent, one cross-section was selected from the highest visible lymph nodes, that is, inguinal and brachial lymph nodes, and discolored parts of the lymph node were selected as ROI (Region of Interest). In the selected parts, signal intensity was measured. Since an overall signal intensity of the acquired MRI images is altered whenever it is measured, it is difficult to evaluate the contrast imaging performance based on an absolute value of the signal intensity (S: signal intensity). For the inguinal lymph node, the right hind leg muscle was used as a control (N: noise). On the other hand, for the brachial lymph node, the right paw muscle was used as a control (N: noise). Compared to the controls, signal to noise ratio (SNR) was calculated. By comparing SNR values before and after using the contrast agent, T2 signal attenuation ratio (ΔR2) was calculated. The results are illustrated by the graphs in FIG. 11. The following Equation 2 is a method for calculation of T2 signal attenuation ratio (ΔR2).

$$T2 \text{ signal attenuation ratio } (\Delta R2) = 100 \times \left[1 - \frac{SNR_t}{SNR_0}\right] \quad \text{[Equation 2]}$$

$SNR_t$(SNR after administration of the contrast agent) =

$$\frac{\text{signal intensity of } ROI \text{ after administration}}{\text{signal intensity of muscle after administration}}$$

$SNR_0$(SNR before administration of the contrast agent) =

$$\frac{\text{signal intensity of } ROI \text{ before administration}}{\text{signal intensity of muscle before administration}}$$

Figure 11:
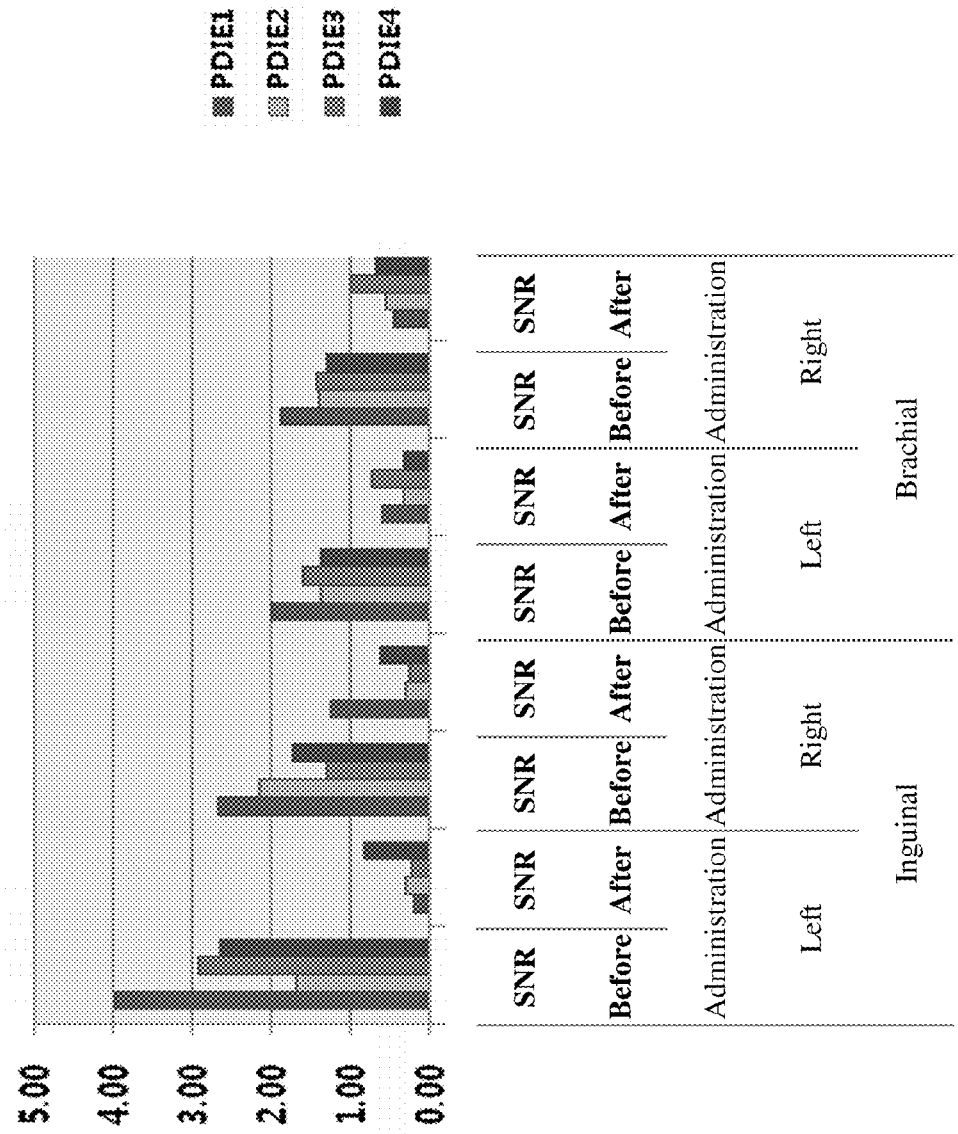
FIG. 11 is a graph showing T2 signal attenuation effects before and after administration of a contrast agent in Example 2.

From FIGS. 7 to 10, it can be seen that the lymph nodes of the nude mouse darkened after administration of the contrast agent. The Tables 5 and 6 include signal to noise ratio (SNR) and signal attenuation ratios (ΔR2) before and after administration of a contrast agent sample to each of the inguinal lymph node and the brachial lymph node. FIG. 11 illustrates the signal to noise ratio (SNR) before and after administration of the contrast agent sample. It was found that signal attenuation after administration of the contrast agent was noticeably high, compared to that before administration thereof.

TABLE 5

T2 signal in inguinal lymph node of a nude mouse by contrast agents

| | Inguinal lymph node | | | | | |
|---|---|---|---|---|---|---|
| | LEFT | | | RIGHT | | |
| Name of sample | Before administration SNR | After administration SNR | Signal attenuation ratio | Before administration SNR | After administration SNR | Signal attenuation ratio |
| PDIE1 contrast agent | 3.94 | 0.21 | 94.8% | 2.68 | 1.26 | 53.0% |
| PDIE2 contrast agent | 1.68 | 0.31 | 81.5% | 2.15 | 0.30 | 86.2% |
| PDIE3 contrast agent | 2.92 | 0.23 | 92.3% | 1.29 | 0.25 | 81.0% |
| PDIE4 contrast agent | 2.65 | 0.84 | 68.5% | 1.74 | 0.63 | 63.9% |

TABLE 6

T2 signal in brachial lymph node of a nude mouse by contrast agents

| | Brachial lymph node | | | | | |
|---|---|---|---|---|---|---|
| | LEFT | | | RIGHT | | |
| Name of sample | Before administration SNR | After administration SNR | Signal attenuation ratio | Before administration SNR | After administration SNR | Signal attenuation ratio |
| PDIE1 contrast agent | 2.01 | 0.61 | 69.5% | 1.87 | 0.46 | 75.6% |
| PDIE2 contrast agent | 1.39 | 0.32 | 76.8% | 1.40 | 0.57 | 59.4% |
| PDIE3 contrast agent | 1.59 | 0.73 | 54.3% | 1.43 | 1.00 | 29.9% |
| PDIE4 contrast agent | 1.37 | 0.33 | 76.1% | 1.30 | 0.68 | 47.7% |

Example 3

Figure 12:
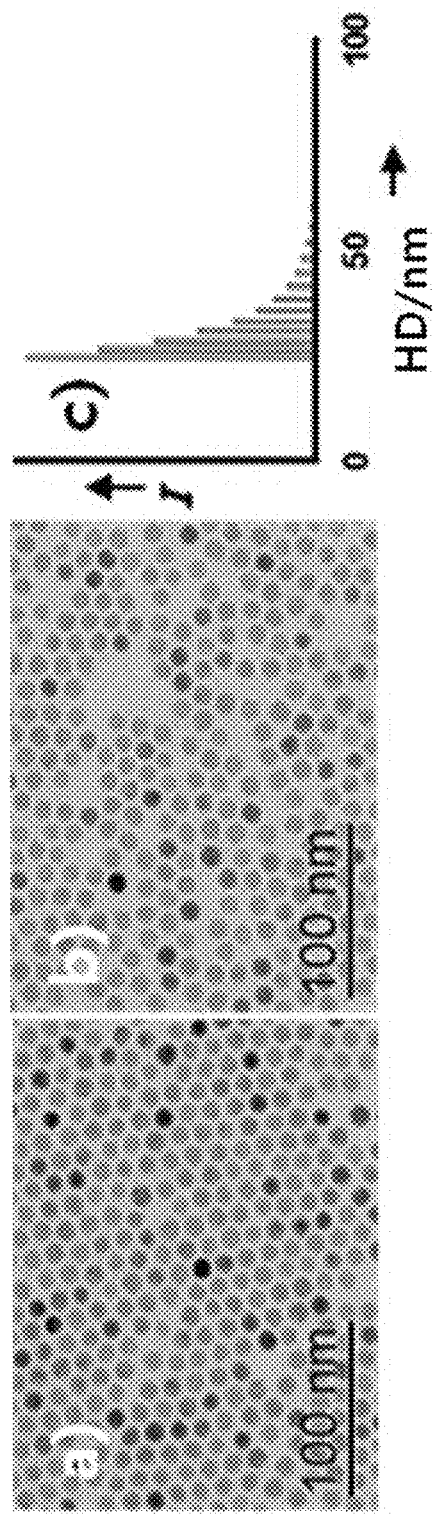
FIG. 12 illustrates transmission electron microscopy (TEM) images of iron oxide nanoparticle (a: 11 nm) dispersed before stabilization, as well as iron oxide nanoparticle colloid (b: 11 nm), which are dispersed in water after stabilization thereof using a mussel adhesive protein-mimetic copolymer (MIL2); and a hydrodynamic diameter (c) of each of the dispersed iron oxide nanoparticle colloids stably dispersed in water by a mussel adhesive protein-mimetic copolymer and by means of a dynamic light scattering (DLS) device.

Determination of Stability of Colloidal Solution Containing Iron Oxide ($Fe_3O_4$) Nanoparticles Stabilized by Mussel Adhesive Protein-Mimetic Copolymer FIG. 12 are TEM photographs illustrating iron oxide ($Fe_3O_4$) nanoparticles before reformed by MIL2 (a) and after reformed by MIL2(b).

According to the TEM photographs in FIG. 12, it can be understood that the iron oxide ($Fe_3O_4$) nanoparticles stably dispersed in water, have substantially the same morphology and size as those of iron oxide ($Fe_3O_4$) nanoparticles dissolved in a hydrophobic solvent. Further, a hydrodynamic diameter of each of the iron oxide ($Fe_3O_4$) nanoparticle colloids is also illustrated in FIG. 12. The hydrodynamic diameter of the iron oxide ($Fe_3O_4$) nanoparticle colloid is a number average hydrodynamic diameter measured by a dynamic light scattering (DLS) method and is observed to be uniform in size.

FIG. 13 illustrates stability of iron oxide ($Fe_3O_4$) nanoparticle colloids stably dispersed in an aqueous medium by a mussel adhesive protein-mimetic copolymer, along with various pH values (a) and ionic concentrations (b). Here, hydrodynamic diameters were measured at various pH values and ionic concentrations through DLS. It can be identified that iron oxide ($Fe_3O_4$) nanoparticle colloids stably dispersed in an aqueous medium using the mussel adhesive protein-mimetic copolymer (MIL1 (▲), MIL2 (○)) are relatively stable at various concentrations and pH values, compared to iron oxide ($Fe_3O_4$) nanoparticles without application of the mussel adhesive protein-mimetic copolymer (MIL0 (♦)).

Example 4

Metastatic Cancer Diagnosis Using the Contrast Agent Including Colloidal Solution of Iron Oxide ($Fe_3O_4$) Nanoparticles Stabilized by Mussel Adhesive Protein-Mimetic Copolymer A colloidal solution of iron oxide ($Fe_3O_4$) nanoparticles stabilized by the mussel adhesive protein-mimetic copolymer was prepared according to the methods in Example 1 and 2.

TABLE 7

Colloidal solution of iron oxide ($Fe_3O_4$) nanoparticles stabilized by mussel adhesive protein-mimetic copolymer for Example 4.

| Name of sample | Diameter of iron oxide nanoparticle (nm) | PEG number average molecular weight | PEI number average molecular weight | Molar ratio PEG | PEI | DOPA | Hydrodynamic diameter (nm) | Dose of administration (mg Fe/kg rabbit) |
|---|---|---|---|---|---|---|---|---|
| PDIE5 colloidal solution | 14 | 5000 | 1800 | 10 | 1 | 20 | 28 | 10.4 |

The colloidal solution in Table 7 was diluted by using a saline solution (0.9% NaCl) for injection, and then a contrast agent having an iron concentration of 6240 ppm and a total volume of 5 mL was prepared while the iron concentration was assayed through ICP-AES and the dose of administration was calculated considering the weight of rabbits. The contrast agent was intravenously injected through an ear of the rabbit. For experiment, metastatic cancer models were established by expressing VX2 cancer cells in iliac lymph nodes of 12 New Zealand white rabbits, and then used to evaluate performance of the contrast agent.

The rabbit with metastatic cancer was weighted about 3 kg. After anesthetizing, the rabbit was horizontally placed in the MRI device (Trio 3.0T, Simens, knee coil), and then cross sections thereof were observed. MRI images of the rabbit were measured before and 24 hours after injecting the contrast agent, and the iliac lymph nodes before and after injecting the contrast agent were observed and compared to each other. The iliac lymph nodes of every rabbits were isolated and stained with hematoxylin-eosin for examination by a pathologist. Specific parameters of the MRI device are as follows.

TR(repetition time)=6.2 msec, TE(echo time)=2.4 msec, FOV=145 mm×145 mm, Matrix size,=129×154, slice thickness=6.0 mm, number of acquisition=1

TABLE 8

Evaluation results for metastatic cancer model rabbits

| Rabbit number | MRI scanning + | Histo-pathology + | MRI scanning − | Histo-pathology − [1] |
|---|---|---|---|---|
| 001 | 3 | 3 | 1 | 1 |
| 002 | 3 | 3 | 2 | 2 |
| 003 | 3 | 3 | 1 | 1 |
| 004 | 1 | 1 | 0 | 0 |
| 005 | 2 | 2 | 1 | 1 |
| 006 | 3 | 3 | 0 | 0 |
| 007 | 1 | 1 | 1 | 1 |
| 008 | 3 | 3 | 2 | 2 |
| 009 | 3 | 3 | 1 | 1 |
| 010 | 2 | 2 | 1 | 1 |

TABLE 8-continued

Evaluation results for metastatic cancer model rabbits

| Rabbit number | MRI scanning + | Histo-pathology + | MRI scanning − | Histo-pathology − [1] |
|---|---|---|---|---|
| 011 | 3 | 3 | 1 | 1 |
| 012 | 2 | 2 | 1 | 1 |
| Total | 29 | 29 | 12 | 12 |
|  | Sensitivity: 100%[2] |  | Specificity: 100%[3] |  |

Figure 14:
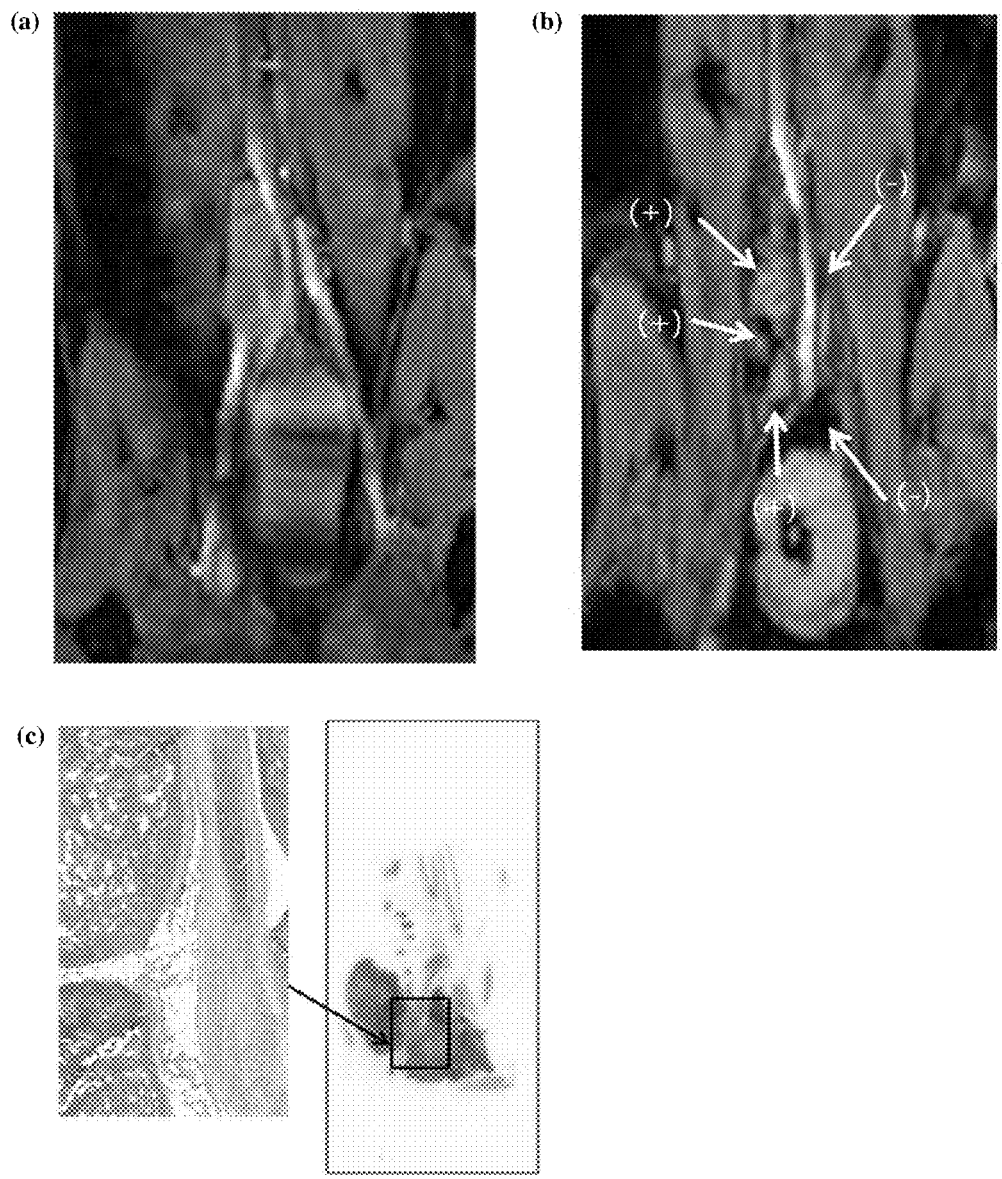
FIG. 14 shows images of contrast enhanced lymphography of metastatic cancer model (a: before injecting the contrast agent, b: after injecting the contrast agent) and result of histopathology (c) of rabbit metastatic cancer models in Example 4.

[1] MRI scanning +: The number of lymph nodes evaluated to be metastatic cancer on the MRI readout
Histopathology +: The number of lymph nodes examined to be metastatic cancer from histopathology results
Image scanning −: The number of lymph nodes evaluated as normal
Histopathology −: The number of lymph nodes examined as normal
[2] Sensitivity: Ratio of the number of lymph nodes evaluated as cancer by MRI scanning to number of lymph nodes examined as cancer by histopathology
[3] Specificity: Ratio of number of normal lymph nodes evaluated by MRI scanning to number of normal lymph nodes examined by histopathology The evaluation results for the metastatic cancer rabbits are shown in Table 8 and FIG. 14. Table 8 shows the number of lymph nodes with metastasis cancer and the number of normal lymph nodes for the 12 rabbits metastatic cancer models. The sensitivity and specificity was 100%, respectively. FIG. 14 shows images of contrast enhanced lymphography and result of histopathology of Rabbit No. 002, before and after injecting the contrast agent. The parts marked in (+) indicate lymph nodes evaluated to be metastatic cancer as the MRI scanning, and the parts marked in (−) indicate lymph nodes examined to be normal as the MRI scanning.

INDUSTRIAL APPLICABILITY

The mussel adhesive protein-mimetic copolymer used in the present invention has multiple units of DOPA in a molecule. DOPA can interact with an inorganic nanoparticle and exhibit high bond strength to the nanoparticles' surface. Additionally, the above copolymer has a positive charge, it may impart electrostatic bonding force to the surface of nanoparticles having a negative charge. Moreover, since numerous polyethyleneglycol molecules having hydrophilic property are bonded to the branches of polyethyleneimine, high aqueous dispersion stabilization may be achieved through hydrophilic property and stereoscopic effects. The PEG on the surface make the iron oxide nanoparticles circulate in the body for a long-time and so many of the iron oxide nanoparticles can reach to the lymph nodes. For better T2 MR imaging, the lymph nodes have to take nanoparticles up as many as possible. So it is crucial of the iron oxide nanoparticles circulate in the body for a long time. The contrast agent including iron oxide nanoparticles reformed by mussel adhesive protein-mimetic copolymer seems to be more taken up and so shows more darkening in the normal lymph nodes and less darkening in the metastatic lymph nodes.

In conclusion, the iron oxide nanoparticles reformed by mussel adhesive protein-mimetic copolymer have a great potential for the detection of lymph node metastasis as a contrast agent for contrast enhanced lymphography.

What is claimed is:

1. A contrast agent for contrast enhanced lymphography, comprising: iron oxide nanoparticles dispersed in an aqueous medium; and polyethyleneimine-graft-(polyethyleneglycol; poly3,4 dihydroxyphenylalanine),
wherein the iron oxide nanoparticles are embedded in a micelle of the polyethyleneimine-graft-(polyethyleneglycol;poly3,4-dihydroxyphenylalanine),
wherein the poly3,4-dihydroxyphenylalanine (PDOPA) is selected from L-PDOPA synthesized from N-carboxyl anhydride of L-DOPA(L-3,4-dihydroxyl phenylalanine) and D-PDOPA synthesized from N-carboxyl anhydride of D-DOPA(D-3,4-dihydroxyl phenylalanine) and L,D-PDOPA synthesized from N-carboxyl anhydride of L,D-DOPA,
wherein the poly3,4-dihydroxyphenylalanine is represented by Structure C,

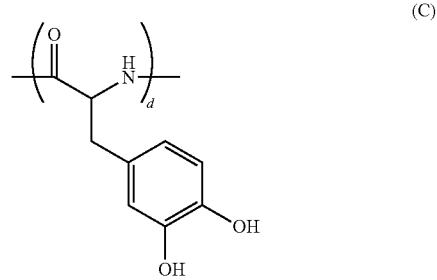

(C)

wherein d ranges from 2 to 100.

2. The contrast agent of claim 1, wherein the iron oxide nanoparticles have a diameter of 1 to 25 nm.

3. The contrast agent of claim 1, wherein the iron oxide nanoparticles dispersed in the aqueous medium have a hydrodynamic diameter of 3 to 100 nm.

4. The contrast agent of claim 1, wherein the polyethyleneglycol has a number average molecular weight of 300 to 50,000 and a hydroxyl group or carboxyl group at one end thereof.

5. The contrast agent of claim 1, wherein the polyethyleneimine is a branch type polyethyleneimine having a number average molecular weight of 100 to 10,100.

6. The contrast agent of claim 1, wherein the polyethyleneglycol is represented by Structure A,

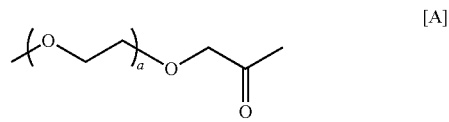

[A]

wherein a ranges from 2 to 1200, wherein the polyethyleneimine is represented by Structure B,

(B)

wherein A is a branched polyethyleneimine and x ranges from 1 to 100.

7. The contrast agent of claim 6, wherein the polyethyleneimine unit is represented by the following structure:

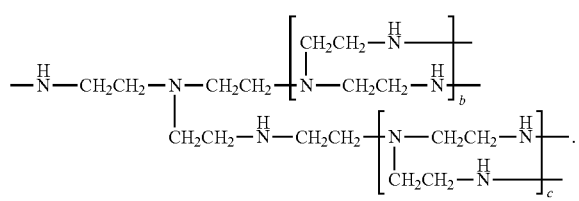

wherein each of b and c ranges from 1 to 100.

8. A method for enhancing contrast in lymphography comprising:
   administering a contrast agent to a subject, wherein the contrast agent comprises:
   iron oxide nanoparticles dispersed in an aqueous medium; and
   a polyethyleneimine-graft-(polyethyleneglycol;poly3,4-dihydroxyphenylalanine), wherein the iron oxide nanoparticles are embedded in a micelle of the polyethyleneimine-graft-(polyethyleneglycol;poly3,4-dihydroxyphenylalanine),
      wherein the poly3,4-dihydroxyphenylalanine is represented by Structure C,

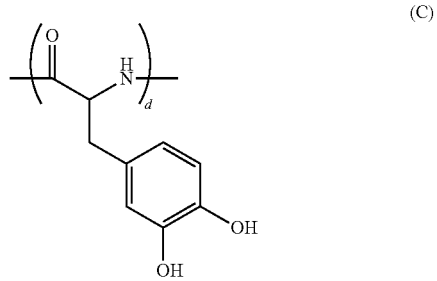

wherein d ranges from 2 to 100.

9. The method of claim 8, which further comprises:
   measuring, prior to the administering the contrast agent, intensity of a first MRI signal of a lymph node;
   measuring, after the administering the contrast agent, a second MRI signal of the lymph node; and
   determining a variation in intensity between the first MRI signal and the second MRI signal.

10. The method of claim 8, wherein the administration of the contrast agent is conducted by intravenous injection.

11. The method of claim 9, wherein the variation in intensity is based on a change in T2 signal intensity.

12. A method for diagnosing cancer of a lymph node comprising:
   administering a contrast agent to a subject; and measuring an MRI signal of lymph nodes,
   wherein the contrast agent comprises:
   iron oxide nanoparticles dispersed in an aqueous medium; and
   a polyethyleneimine-graft-(polyethyleneglycol;poly3,4-dihydroxyphenylalanine), wherein the iron oxide nanoparticles are embedded in a micelle of the polyethyleneimine-graft-(polyethyleneglycol;poly3,4-dihydroxyphenylalanine),
      wherein the poly3,4-dihydroxyphenylalanine is represented by Structure C, wherein d ranges from 2 to 100.

* * * * *